United States Patent
Yamauchi et al.

(10) Patent No.: US 9,372,331 B2
(45) Date of Patent: Jun. 21, 2016

(54) OBSERVATION DEVICE

(71) Applicants: HAMAMATSU PHOTONICS K.K., Hamamatsu-shi, Shizuoka (JP); Mechanojenic Japan, K.K., Tokyo (JP)

(72) Inventors: Toyohiko Yamauchi, Hamamatsu (JP); Hidenao Iwai, Hamamatsu (JP); Makoto Funaki, Media, PA (US)

(73) Assignees: HAMAMATSU PHOTONICS K. K., Hamamatsu-shi, Shizuoka (JP); Mechanojenic Japan, K. K., Tokyo (JP)

( * ) Notice: Subject to any disclaimer, the term of this patent is extended or adjusted under 35 U.S.C. 154(b) by 0 days.

(21) Appl. No.: 14/419,714

(22) PCT Filed: Aug. 7, 2013

(86) PCT No.: PCT/JP2013/071373
§ 371 (c)(1),
(2) Date: Feb. 5, 2015

(87) PCT Pub. No.: WO2014/024923
PCT Pub. Date: Feb. 13, 2014

(65) Prior Publication Data
US 2015/0198795 A1 Jul. 16, 2015

(30) Foreign Application Priority Data

Aug. 8, 2012 (JP) ................. 2012-175902

(51) Int. Cl.
*G02B 21/06* (2006.01)
*G02B 21/00* (2006.01)
(Continued)

(52) U.S. Cl.
CPC ........ *G02B 21/0076* (2013.01); *G01N 21/6458* (2013.01); *G02B 21/06* (2013.01); *G02B 21/14* (2013.01); *G02B 21/16* (2013.01); *G02B 21/18* (2013.01); *G01N 2021/6441* (2013.01); *G02B 21/0056* (2013.01)

(58) Field of Classification Search
CPC .... G02B 21/18; G02B 21/0032; G02B 21/00; G02B 21/06; G02B 21/0076; G02B 21/0056; G02B 5/32; G02B 2290/70; G01N 21/45; G01N 21/64; G01B 9/02081; G03F 9/7049
USPC ................................. 359/384, 385
See application file for complete search history.

(56) References Cited

U.S. PATENT DOCUMENTS 6,496,267 B1 12/2002 Takaoka
2007/0263282 A1* 11/2007 Takamizawa et al. ........... G02B 21/0032 359/384

FOREIGN PATENT DOCUMENTS

JP 2000-292705 A 10/2000
JP 2001-091821 A 4/2001
(Continued)

OTHER PUBLICATIONS

Hidenao Iwai, et al., "Quantitative phase imaging using actively stabilized phase-shifting low-coherence interferometry," Optics Letters, vol. 29, No. 20, 2004, pp. 2399-2401.
(Continued)

*Primary Examiner* — Euncha Cherry
(74) *Attorney, Agent, or Firm* — Drinker Biddle & Reath LLP

(57) ABSTRACT

The observation device 1 is a device capable of substantially simultaneously acquiring the fluorescence image and the interference image on the common observation plane in the observation object 90 mounted on slide glass 41, and has an excitation light source 11, a filter 12, a dichroic mirror 13, a lens 14, a dichroic mirror 15, an objective lens 16, a filter 17, a fluorescence imaging unit 18, an interference imaging light source 21, a filter 22, a dichroic mirror 23, a lens 24, a half mirror 25, an objective lens 26, a lens 27, a dichroic mirror 28, an interference imaging unit 29, a position detection light source 31, a light detection unit 32, the slide glass 41, an actuator 42, a reference mirror 43, an actuator 44, a control unit 51, and a display unit 52.

13 Claims, 22 Drawing Sheets

(51) Int. Cl.
    *G01N 21/64*     (2006.01)
    *G02B 21/14*     (2006.01)
    *G02B 21/16*     (2006.01)
    *G02B 21/18*     (2006.01)

(56) References Cited

FOREIGN PATENT DOCUMENTS

| | | |
|---|---|---|
| JP | 2006-003543 A | 1/2006 |
| JP | 2006-195240 A | 7/2006 |

OTHER PUBLICATIONS

Toyohiko Yamauchi, et al., "Low-coherent quantitative phase microscope for nanometer-scale measurement of living cells morphology," Optics Express, vol. 16, No. 16, 2008, pp. 12227-12238.

English-language translation of International Preliminary Report on Patentability (IPRP) dated Feb. 19, 2015 that issued in WO Patent Application No. PCT/JP2013/071373.

* cited by examiner

OBSERVATION DEVICE

TECHNICAL FIELD

The present invention relates to an observation device.

BACKGROUND ART

The invention of observation apparatus designed to observe an observation object on an observation plane at a desired position in an optical-axis direction of an objective lens is disclosed in Patent Literatures 1 and 2. The observation apparatus disclosed in these Literatures is configured to detect a front face or a back face of slide glass as a reference observation plane by making use of the large intensity of reflection from the front face or the back face of the slide glass with the observation object thereon, to move the slide glass in the optical-axis direction by a distance between a desired observation plane in the observation object and the reference observation plane, and then to observe the observation object on the desired observation plane.

For example, when the observation object is a cell, an observer sometimes desires to acquire physiological information of the observation object and sometimes desires to acquire morphological information of the observation object. For acquiring the physiological information of the observation object, a specific part in the observation object is labeled with a fluorochrome, the observation object is irradiated with excitation light, and an image of fluorescence generated upon the irradiation is taken. On the other hand, for acquiring the morphological information of the observation object, low-coherence light is split into two beams as a first branch beam and a second branch beam, interference is caused between first reflection made upon application of the first branch beam onto the observation object and second reflection made upon application of the second branch beam onto a reference mirror, and a resultant interference image between them is taken (cf. Non Patent Literatures 1 and 2).

CITATION LIST

Patent Literatures

Patent Literature 1: Japanese Patent Application Laid-Open Publication No. 2006-3543
Patent Literature 2: Japanese Patent Application Laid-Open Publication No. 2001-91821

Non Patent Literatures

Non Patent Literature 1: H. Iwai, C. Fang-Yen, G. Popescu, A. Wax, K. Badizadegan, R. R. Dasari, and M. S. Feld, "Quantitative phase imaging using actively stabilized phase-shifting low-coherence interferometry," Opt. Lett. Vol. 29 No. 20 pp. 2399-2401 (2004)
Non Patent Literature 2: T. Yamauchi, H. Iwai, M. Miwa, and Y. Yamashita, "Low-coherent quantitative phase microscope for nanometer-scale measurement of living cells morphology," Opt. Express Vol. 16 No. 16 pp. 12227-12238 (2008)

SUMMARY OF INVENTION

Technical Problem

Incidentally, if the physiological information and the morphological information of the observation object can be acquired substantially at the same time, we can expect to gain a variety of useful knowledge on the observation object. It is difficult, however, to acquire the fluorescence image and the interference image on a common observation plane in the observation object, only by simply combining an observation device for taking the fluorescence image and an observation device for taking the interference image.

One aspect of the present invention has been accomplished at least in order to solve the above problem and an object thereof is to provide an observation device capable of readily acquiring the fluorescence image and the interference image on the common observation plane in the observation object substantially at the same time.

Solution to Problem

An observation device according to one aspect of the present invention comprises: (1) an excitation light source for outputting excitation light; (2) an objective lens for implementing irradiation of an observation object with the excitation light output from the excitation light source and receiving fluorescence generated in the observation object in accordance with the irradiation; (3) a fluorescence imaging unit for taking an image of the fluorescence generated in the observation object and guided through the objective lens; (4) a mount unit for the observation object to be mounted thereon, which is movable in an optical-axis direction of the objective lens; (5) an interference imaging light source for outputting interference imaging light; (6) a position detection light source for outputting position detection light; (7) a multiplexing unit for multiplexing the interference imaging light output from the interference imaging light source and the position detection light output from the position detection light source and outputting the light multiplexed; (8) an interference optical system for splitting the light multiplexed and output by the multiplexing unit, into two beams and outputting the two beams as a first branch beam and a second branch beam, for implementing application of the first branch beam through the objective lens onto the observation object or onto the mount unit and receiving input of first reflection generated in accordance with the application, for implementing application of the second branch beam onto a reference mirror and receiving input of second reflection generated in accordance with the application, and for letting the first reflection and the second reflection interfere with each other and outputting resultant light; (9) a demultiplexing unit for demultiplexing the light output from the interference optical system into the interference imaging light and the position detection light and outputting the interference imaging light and the position detection light; (10) an interference imaging unit for taking an interference image of the interference imaging light output from the demultiplexing unit; (11) a light detection unit for implementing detection of interference intensity of the position detection light output from the demultiplexing unit; and (12) a control unit for acquiring the result of the detection by the light detection unit and for controlling a positioning operation of the mount unit, an imaging operation by the fluorescence imaging unit, and an imaging operation by the interference imaging unit.

Furthermore, in the observation device according to one aspect of the present invention, the control unit performs as follows: the control unit determines an optical path length difference between an optical path of the position detection light from the position detection light source via the mount unit to the light detection unit and an optical path of the position detection light from the position detection light source via the reference mirror to the light detection unit, based on the result of the detection of the interference intensity by the light detection unit; the control unit performs feedback control based on the optical path length difference thus determined, thereby to set a position of the mount unit to a target position; the control unit makes both or either one of the imaging operation by the fluorescence imaging unit and the imaging operation by the interference imaging unit carried out at the target position of the mount unit.

In the observation device according to one aspect of the present invention, the position detection light output from the position detection light source can be guided through the objective lens to be applied to a position on the mount unit where the observation object is absent. The control unit can make the imaging operation by the fluorescence imaging unit or the imaging operation by the interference imaging unit carried out at each of a plurality of target positions of the mount unit to acquire two-dimensional fluorescence images or two-dimensional interference images, and acquire a three-dimensional fluorescence image or a three-dimensional interference image of the observation object, based on the images. The control unit can obtain an interference intensity image or an interference phase image, based on the interference image taken by the interference imaging unit. The observation device according to one aspect of the present invention can further comprise a display unit for displaying the fluorescence image taken by the fluorescence imaging unit and the interference image taken by the interference imaging unit.

In the observation device according to one aspect of the present invention, the control unit can make the imaging operation by the fluorescence imaging unit and the imaging operation by the interference imaging unit carried out at each of a plurality of target positions of the mount unit to acquire two-dimensional fluorescence images and two-dimensional interference images in synchronism, and acquire a three-dimensional fluorescence image and a three-dimensional interference image of the observation object, based on the images.

The observation device according to one aspect of the present invention can be configured as follows: at each of a plurality of target positions of the mount unit, an object of a known shape is used as a standard object, with which the imaging operation by the fluorescence imaging unit and the imaging operation by the interference imaging unit are made to be carried out to acquire a three-dimensional fluorescence image and a three-dimensional interference image of the standard object; when there is a difference in relative position in the optical-axis direction between the three-dimensional fluorescence image and the three-dimensional interference image, the fluorescence imaging unit is moved in the optical-axis direction, thereby to finely adjust the optical system so as to eliminate the difference in relative position between the three-dimensional fluorescence image and the three-dimensional interference image, followed by execution of imaging of a variety of observation objects.

The observation device according to one aspect of the present invention can be configured as follows: at each of a plurality of target positions of the mount unit, an object of a known shape is used as a standard object, with which the imaging operation by the fluorescence imaging unit and the imaging operation by the interference imaging unit are made to be carried out to acquire a three-dimensional fluorescence image and a three-dimensional interference image of the standard object, and wherein when there is a difference in relative position in the optical-axis direction between the three-dimensional fluorescence image and the three-dimensional interference image, a lens which can be moved independently of a focusing condition of the interference image, out of lenses for focusing the fluorescence image, is moved in the optical-axis direction, thereby to finely adjust the optical system so as to eliminate the difference in relative position between the three-dimensional fluorescence image and the three-dimensional interference image, followed by execution of imaging of a variety of observation objects.

The observation device according to one aspect of the present invention can be configured so that the excitation light source and the fluorescence imaging unit have a configuration of a confocal microscope. The observation device according to one aspect of the present invention can also be configured so that the excitation light source is a short pulse laser with a pulse duration of not more than 1000 femtoseconds and so that the excitation light source and the fluorescence imaging unit have a configuration of a two-photon excitation microscope. The observation device according to one aspect of the present invention can also be configured so that the fluorescence imaging unit images fluorescence attributed to fluorescence resonance energy transfer in the observation object.

The observation device according to one aspect of the present invention can be configured so that a granular object inside the observation object is fluorescently stained and so that a plurality of three-dimensional fluorescence images and three-dimensional interference images of the observation object are taken in time series, to visualize a relative positional relation between the fluorescently-stained granular object and a film-like structure on a surface or inside of the observation object.

The observation device according to one aspect of the present invention can be configured as follows: at a start of observation, the irradiation with the excitation light by the excitation light source is carried out and the imaging operation by the fluorescence imaging unit and the imaging operation by the interference imaging unit are carried out, only for a duration of time shorter than an overall time duration of observation; correspondence is made between a fluorescently-labeled object and an object resulting from feature extraction by interference imaging, from images obtained by the operations; after completion of the imaging at the start of observation, the irradiation with the excitation light by the excitation light source is not carried out and only the imaging operation by the interference imaging unit is carried out, thereby to perform temporal observation of the fluorescently-labeled object.

Advantageous Effect of Invention

The observation device according to one aspect of the present invention can readily acquire the fluorescence image and the interference image on the common observation plane in the observation object substantially at the same time.

DESCRIPTION OF EMBODIMENTS

An embodiment of the present invention will be described below in detail with reference to the accompanying drawings. The same elements will be denoted by the same reference signs in the description of the drawings, without redundant description.

Figure 1:
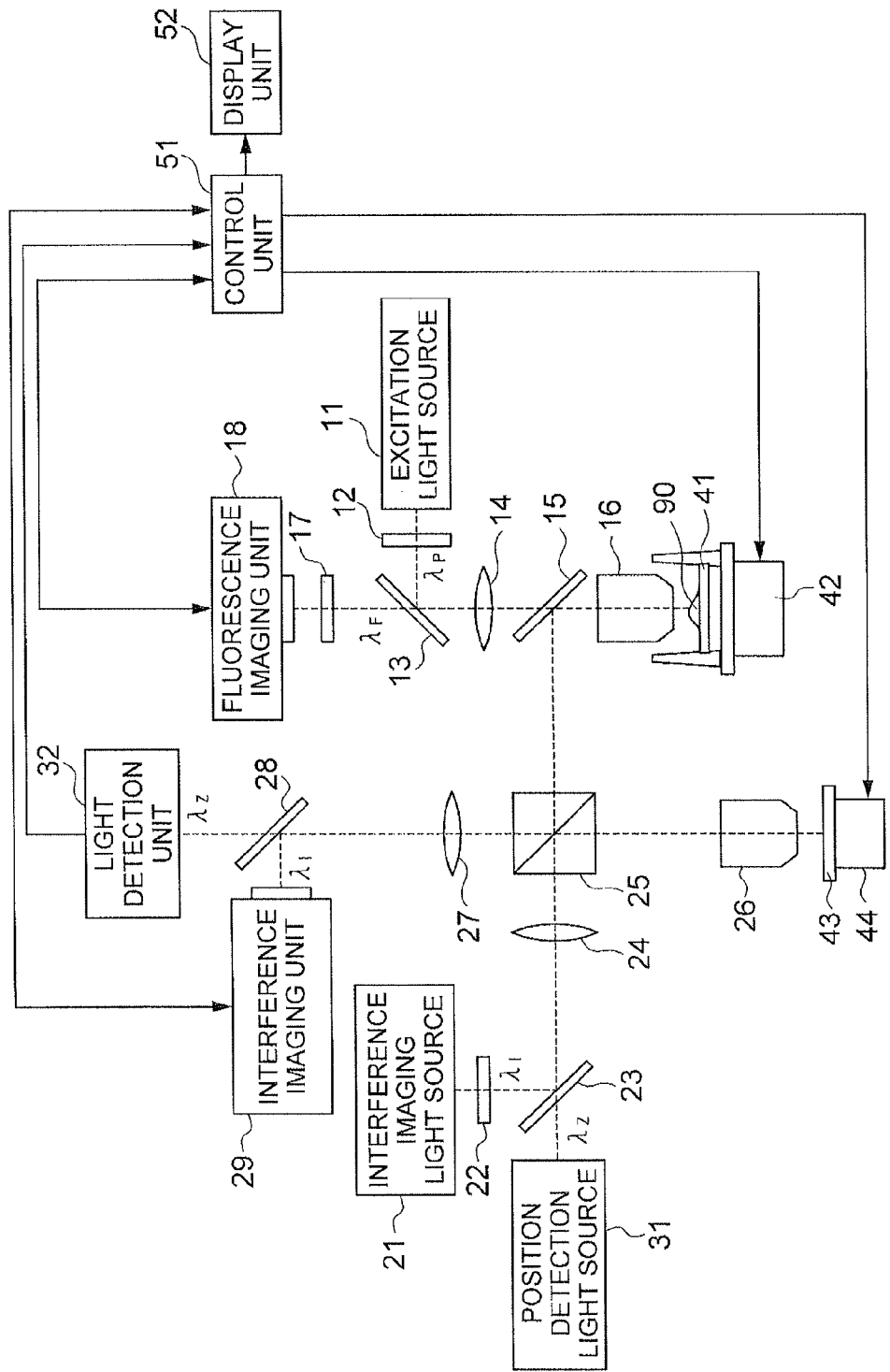
FIG. 1 is a drawing showing a configuration of an observation device 1 of an embodiment of the present invention.

FIG. 1 is a drawing showing a configuration of an observation device 1 of the present embodiment. The observation device 1 is a device capable of acquiring a fluorescence image and an interference image on a common observation plane in an observation object 90 mounted on slide glass 41, substantially at the same time, and has an excitation light source 11, a filter 12, a dichroic mirror 13, a lens 14, a dichroic mirror 15, an objective lens 16, a filter 17, a fluorescence imaging unit 18, an interference imaging light source 21, a filter 22, a dichroic mirror 23, a lens 24, a half mirror 25, an objective lens 26, a lens 27, a dichroic mirror 28, an interference imaging unit 29, a position detection light source 31, a light detection unit 32, the slide glass 41, an actuator 42, a reference mirror 43, an actuator 44, a control unit 51, and a display unit 52.

The observation object 90 is, for example, a cell and a specific part in the observation object 90 is labeled with a fluorochrome. The excitation light source 11 outputs excitation light $L_P$ of wavelength $\lambda_P$ which can excite the fluorochrome. The excitation light source 11 can be a laser light source and can also be any other light source. The filter 12 selectively transmits the excitation light of the specific wavelength $\lambda_P$ out of the light output from the excitation light source 11. The dichroic mirror 13 reflects the excitation light $L_P$ having arrived from the filer 12 and transmits fluorescence $L_F$ of wavelength $\lambda_F$ generated in the observation object 90. The dichroic mirror 15 transmits the excitation light $L_P$ having arrived through the lens 14 after reflected by the dichroic mirror 13, transmits the fluorescence $L_F$ generated in the observation object 90, and reflects light output from each of the interference imaging light source 21 and the position detection light source 31.

The objective lens 16 irradiates the observation object 90 mounted on the slide glass 41, with the excitation light $L_P$ having been output from the excitation light source 11 and having traveled via the filter 12, dichroic mirror 13, lens 14, and dichroic mirror 15. The objective lens 16 receives the fluorescence $L_F$ generated in the observation object 90 in accordance with the irradiation of the observation object 90 with the excitation light $L_P$. The objective lens 16 irradiates the slide glass 41 or the observation object 90 with the light having been output from each of the interference imaging light source 21 and the position detection light source 31 and reflected by the dichroic mirror 15. Furthermore, the objective lens 16 receives reflection generated on the slide glass 41 or on the observation object 90 in accordance with the irradiation with each of these light beams.

The filter 17 selectively transmits the fluorescence $L_F$, out of light having been generated in the observation object 90 and having arrived through the objective lens 16, dichroic mirror 15, lens 14, and dichroic mirror 13, and blocks light of the other wavelengths. The fluorescence imaging unit 18 can receive the fluorescence $L_F$ having arrived through the filter 17 and take an image of the fluorescence $L_F$ generated in the observation object 90. If the focusing optical system for the fluorescence $L_F$ from the objective lens 16 to an imaging screen of the fluorescence imaging unit 18 is fixed, the fluorescence imaging unit 18 can acquire the fluorescence image on an observation plane at a position (and near it) of a fixed distance along the optical-axis distance from the objective lens 16.

The excitation light source 11 and the fluorescence imaging unit 18 can also have a configuration of a confocal microscope. The excitation light source 11 is a short pulse laser with the pulse duration of not more than 1000 femtoseconds and the excitation light source 11 and the fluorescence imaging unit 18 can also have a configuration of a two-photon excitation microscope. Furthermore, the fluorescence imaging unit 18 can also image fluorescence attributed to fluorescence resonance energy transfer in the observation object 90.

The interference imaging light source 21 outputs interference imaging light $L_I$ of wavelength $\lambda_I$. The interference imaging light $L_I$ can be low-coherent light. The interference imaging light source 21 can be, for example, a halogen lamp or a white high-luminance LED. The filter 22 selectively transmits the interference imaging light of the specific wavelength $\lambda_I$ out of the light output from the interference imaging light source 21.

The position detection light source 31 outputs position detection light $L_Z$ of wavelength $\lambda_Z$. The position detection light $L_Z$ can be generally high-coherent light. The position detection light source 31 can be a laser light source and can also be an SLD (Super Luminescent Diode) or the like capable of outputting light with a wavelength bandwidth of several nm.

Figure 2:
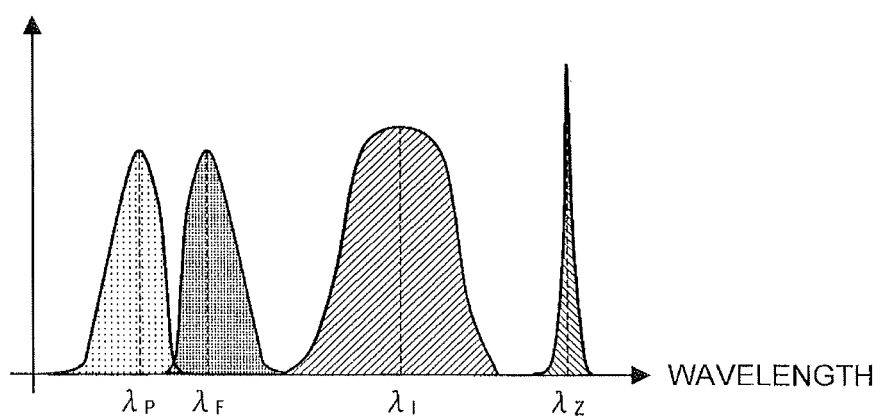
FIG. 2 is a drawing showing an example of spectra of wavelengths of respective light beams used in the observation device 1 of the embodiment of the present invention.

It is noted that the wavelength $\lambda_P$ of the excitation light output from the excitation light source 11, the wavelength $\lambda_F$ of the fluorescence generated in the observation object 90, the wavelength $\lambda_I$ of the interference imaging light output from the interference imaging light source 21, and the wavelength $\lambda_Z$ of the position detection light output from the position detection light source 31 do not agree with each other, as shown in an example of spectra in FIG. 2.

The dichroic mirror 23 acts as a multiplexing unit that reflects the interference imaging light $L_I$ having been output from the interference imaging light source 21 and having arrived through the filter 22, transmits the position detection light $L_Z$ output from the position detection light source 31, multiplexes these beams of interference imaging light $L_I$ and position detection light $L_Z$, and outputs the light thus multiplexed.

The half mirror 25 acts as an interference optical system. Namely, the half mirror 25 splits the multiplexed light (interference imaging light $L_I$ and position detection light $L_Z$) having been multiplexed and output by the dichroic mirror 23 and having arrived through the lens 24, into two beams as a first branch beam and a second branch beam, outputs the first branch beam to the dichroic mirror 15, and outputs the second branch beam to the objective lens 26. The first branch beam travels via the dichroic mirror 15 and the objective lens 16 to be applied onto the observation object 90 or onto the slide glass 41. First reflection generated in accordance with the application of this first branch beam travels via the objective lens 16 and the dichroic mirror 15 to reach the half mirror 25. The second branch beam travels via the objective lens 26 to be applied onto the reference mirror 43 and second reflection generated in accordance with the application of this second branch beam travels via the objective lens 26 to reach the half mirror 25. Then the half mirror 25 receives input of the first reflection generated on the observation object 90 or on the slide glass 41 and input of the second reflection generated on the reference mirror 43, lets these first reflection and second reflection interfere with each other, and outputs resultant light to the lens 27.

In the description hereinbelow, a first optical path is defined as an optical path of the first branch beam from the half mirror 25 through the objective lens 16 to a certain observation plane and an optical path of the first reflection from the observation plane through the objective lens 16 to the half mirror 25 together. Furthermore, a second optical path is defined as an optical path of the second branch beam from the half mirror 25 through the objective lens 26 to a reflective surface of the reference mirror 43 and an optical path of the second reflection from the reflective surface of the reference mirror 43 through the objective lens 26 to the half mirror 25 together.

The position detection light $L_Z$ included in the first branch beam applied from the half mirror 25 via the objective lens 16 can be applied onto the surface of the slide glass 41 where the observation object 90 is absent in the field of the objective lens 16. Furthermore, the surface of the slide glass 41 may be coated with a reflection-enhancing coating for the wavelength of the position detection light $L_Z$.

The dichroic mirror 28 receives light having been output from the half mirror 25 and having arrived through the lens 27, reflects the interference imaging light $L_I$ out of the light to the interference imaging unit 29, and transmits the position detection light $L_Z$ to the light detection unit 32. The dichroic mirror 28 acts as a demultiplexing unit that demultiplexes the incident light into the interference imaging light $L_I$ and the position detection light $L_Z$ and outputs them.

The interference imaging unit 29 takes an interference image of the interference imaging light $L_I$ reflected by the dichroic mirror 28. When as to a certain observation plane a difference between respective optical path lengths of the first optical path and the second optical path is not more than about the coherent length of the interference imaging light $L_I$, the reflection $L_I$ from the observation plane interferes with the reflection $L_I$ from the reference mirror 43 and, for this reason, the interference imaging unit 29 can take the interference image of the observation plane.

The light detection unit 32 detects the interference intensity of the position detection light $L_Z$ transmitted by the dichroic mirror 28. The slide glass 41 (mount unit) for the observation object 90 to be mounted thereon is movable in the optical-axis direction of the objective lens 16 by the actuator 42. The reference mirror 43 is movable in the optical-axis direction of the objective lens 26 by the actuator 44. As the respective positions of the slide glass 41 and the reference mirror 43 change, the interference intensity detected by the light detection unit 32 varies as well.

The control unit 51 can obtain an optical path length difference between the optical path of the position detection light $L_Z$ from the position detection light source 31 via the slide glass 41 to the light detection unit 32 and the optical path of the position detection light $L_Z$ from the position detection light source 31 via the reference mirror 43 to the light detection unit 32, based on the result of the detection of the interference intensity by the light detection unit 32. Then the control unit 51 can perform a positioning operation of the slide glass 41. The control unit 51 performs feedback control based on the obtained optical path length difference to set the position of the slide glass 41 to a target position, and implements both or either one of an imaging operation by the fluorescence imaging unit 18 and an imaging operation by the interference imaging unit 29 at the target position of the slide glass 41.

The control unit 51 acquires the fluorescence image obtained by the imaging by the fluorescence imaging unit 18 and acquires the interference image obtained by the imaging by the interference imaging unit 29. The display unit 52 displays the fluorescence image and the interference image. The display unit 52 can display the fluorescence image and the interference image as arranged right and left on a screen or can display the fluorescence image and the interference image as superimposed on each other.

The control unit 51 can make the imaging operation by the fluorescence imaging unit 18 or the imaging operation by the interference imaging unit 29 carried out at each of a plurality of target positions (which can be a plurality of target positions at constant intervals) of the slide glass 41 to acquire two-dimensional fluorescence images or two-dimensional interference images, whereby it can also acquire a three-dimensional fluorescence image or a three-dimensional interference image of the observation object 90, based on these images. In this case, the display unit 52 can display a two-dimensional fluorescence image or a two-dimensional interference image on any desired plane in the observation object 90 (e.g., a plane parallel to the optical axis of the objective lens 16).

Furthermore, the control unit 51 can make the imaging operation by the fluorescence imaging unit 18 and the imaging operation by the interference imaging unit 29 carried out at each of a plurality of target positions of the slide glass 41 to acquire two-dimensional fluorescence images and two-dimensional interference images in synchronism, whereby it can also acquire a three-dimensional fluorescence image and a three-dimensional interference image of the observation object 90, based on these images.

The observation device 1 can be configured so as to vary the optical path length difference between the first optical path and the second optical path only by change of the distance between the objective lens 16 and the observation object 90. For that configuration, the dichroic mirror 15, objective lens 16, half mirror 25, objective lens 26, actuator 42, and actuator 44 can be fixed on a common rigid base.

Figure 3:
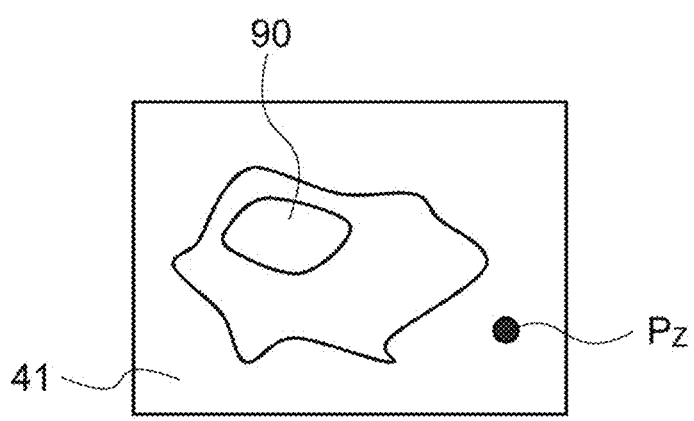
FIG. 3 is a drawing showing an observation object 90 and an irradiation position $P_Z$ of a position detection light beam $L_Z$ in a field of an objective lens 16.

The following will describe a method for monitoring the position of the slide glass 41 by the position detection light source 31 and the light detection unit 32 and performing feedback control thereof. FIG. 3 is a drawing showing the observation object 90 and the irradiation position $P_Z$ of the position detection light $L_Z$ in the field of the objective lens 16. As shown in FIG. 3, when the observation object 90 is a cell, the position detection light $L_Z$ is not applied to the observation object 90, so as to keep the detection result unchanged with motion of the observation object 90, but it is applied normally to the irradiation position $P_Z$ on the slide glass 41 where the observation object 90 is absent. The irradiation position $P_Z$ of the position detection light $L_Z$ can also be a position off the slide glass 41 or can also be a part moved along with the slide glass 41 by the actuator 42.

Figure 4:
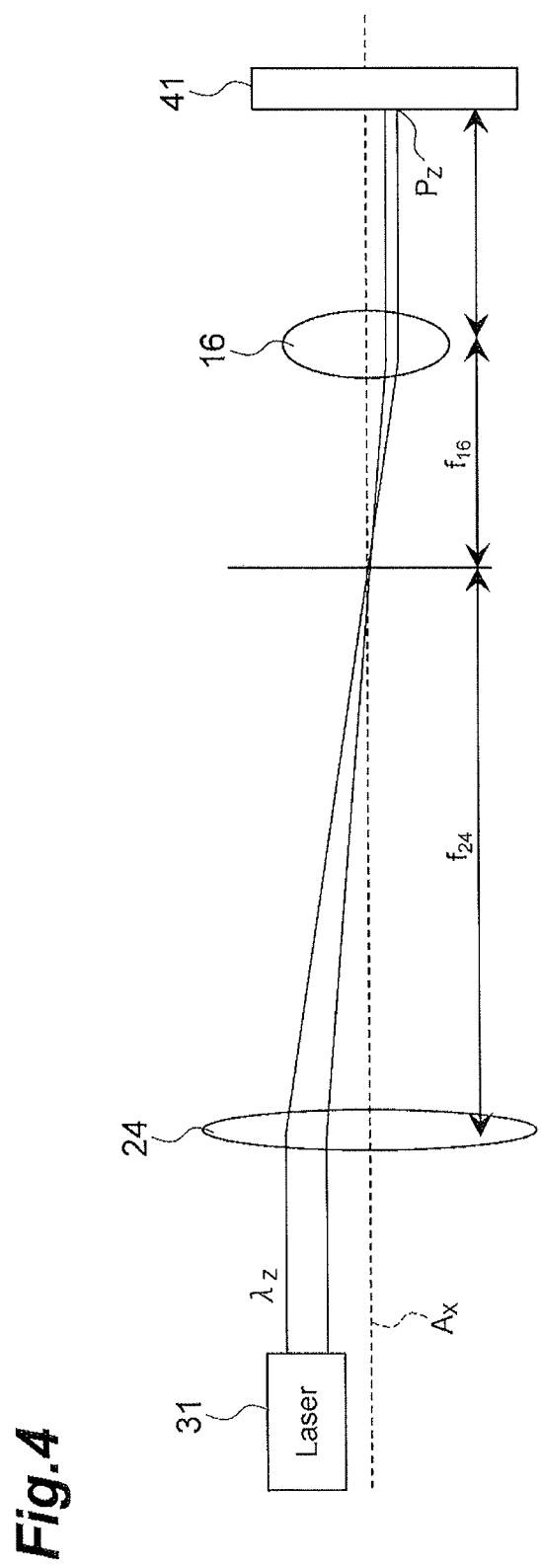
FIG. 4 is a drawing showing an optical system for the position detection light beam $L_Z$ from a position detection light source 31 to slide glass 41.

FIG. 4 is a drawing showing the optical system for the position detection light $L_Z$ from the position detection light source 31 to the slide glass 41. FIG. 4 is drawn without illustration of the dichroic mirror 23, half mirror 25, and dichroic mirror 15 on the optical system for the position detection light $L_Z$. Let $f_{24}$ be the focal length of the lens 24 and $f_{15}$ be the focal length of the objective lens 16. For example, the focal length $f_{24}$ of the lens 24 is approximately 200 mm and the focal length $f_{16}$ of the objective lens 16 approximately 10 mm.

The optical system for the position detection light $L_Z$ is set so that the optical path length between the lens 24 and the objective lens 16 is $f_{24}+f_{16}$. The position detection light source 31 is arranged at a position off the optical axis $A_X$ of the optical system for the position detection light $L_Z$ in the direction normal thereto and outputs the position detection light $L_Z$ in a direction parallel to the optical axis $A_X$.

As the optical system for the position detection light $L_Z$ from the position detection light source 31 to the slide glass 41 is set as described above, the position detection light $L_Z$ output from the position detection light source 31 is once focused by the lens 24, thereafter diverges to enter the objective lens 16, and is collimated by this objective lens 16, whereby the position detection light $L_Z$ can be applied normally to the irradiation position $P_Z$ on the slide glass 41 where the observation object 90 is absent. By this, the observation object 90 can be arranged in a central region in the field of the objective lens 16 and the position detection light $L_Z$ can be normally applied to the irradiation position $P_Z$ on the slide glass 41 where the observation object 90 is absent.

Whether the position detection light $L_Z$ is normally incident to the slide glass 41 can be confirmed as described below. A mirror is located in place of the dichroic mirror 28 and the position detection light $L_Z$ is reflected by this mirror to enter the interference imaging unit 29, whereby the irradiation position $P_Z$ of the position detection light $L_Z$ in the field of the objective lens 16 can be observed by the interference imaging unit 29. When the irradiation position $P_Z$ of the position detection light $L_Z$ observed by the interference imaging unit 29 is still with vertical movement of the slide glass 41 by the actuator 42, the position detection light $\lambda_Z$ is determined to be normally incident to the slide glass 41. If the irradiation position $P_Z$ of the position detection light $L_Z$ observed by the interference imaging unit 29 is not still, the direction of arrangement of the position detection light source 31 will be adjusted. If the interference imaging unit 29 does not have sufficient sensitivity to the wavelength $L_Z$, the light is converted into light of a wavelength to which the interference imaging unit 29 has sufficient sensitivity, by a wavelength conversion element set in front of a light receiving surface of the interference imaging unit 29.

The position of the slide glass 41 can be monitored based on the result of detection of interference intensity of the position detection light $L_Z$ by the light detection unit 32. Specifically, the position of the slide glass 41 can be controlled by feedback control while monitoring the position, using zero-cross points of interference intensity of the position detection light $L_Z$ by the light detection unit 32. For example, as described in Non Patent Literature 1, the actuator 44 is vertically moved in a sinusoidal pattern with a small amplitude (e.g., the amplitude of about 10 nm) and a high frequency (e.g., the frequency of not less than 3 kHz) along the optical axis of the objective lens 26 to modulate an output signal of the light detection unit 32 and this output signal of the light detection unit 32 is demodulated, whereby the position of the slide glass 41 can be controlled with accuracy of one-several hundredth of the wavelength $\lambda_Z$ by feedback control while monitoring it.

Figure 5:
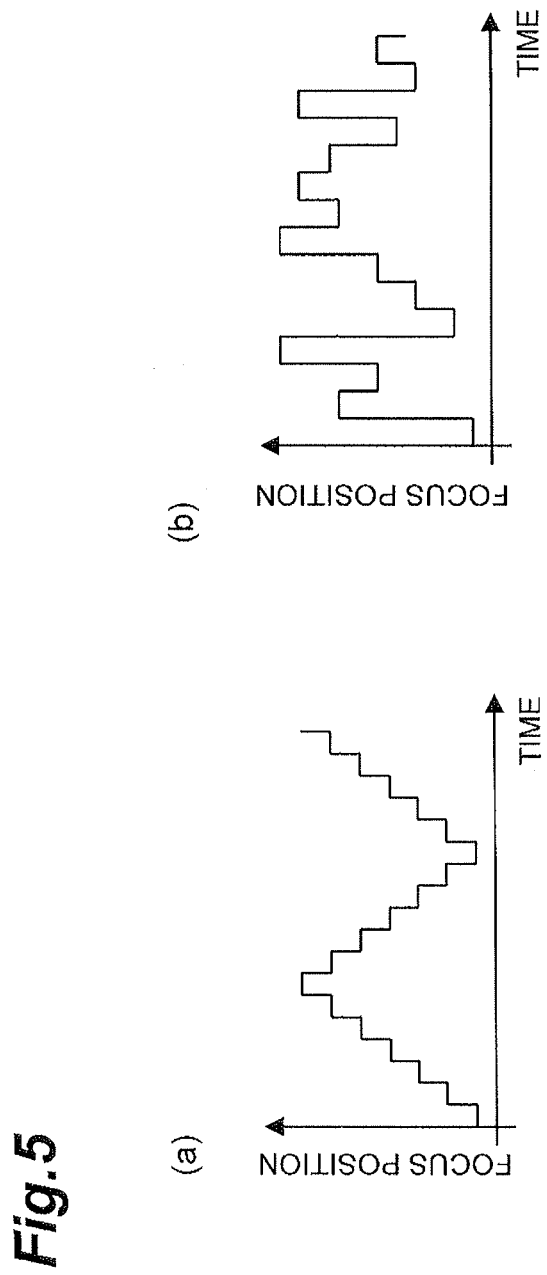
FIG. 5 is a drawing showing examples of temporal change of position of the slide glass 41.

FIG. 5 is a drawing showing examples of temporal change of the position of the slide glass 41. Since the position of the slide glass 41 can be highly accurately monitored and feedback-controlled by means of the position detection light source 31 and the light detection unit 32, the position of the slide glass 41 can be sequentially set along the optical axis of the objective lens 16 as shown in Part (a) of FIG. 5 or the position of the slide glass 41 can also be set at random along the optical axis of the objective lens 16 as shown in Part (b) of FIG. 5, depending upon applications necessary for the observation object 90. In the latter case, for example, it is also possible to implement random access in an appropriate order to focus planes where physiologically interesting signals are obtained in the observation object 90.

The following will describe a method for acquiring a fluorescence image and an interference image on a common observation plane in the observation object 90 substantially at the same time. The fluorescence image obtained by the fluorescence imaging unit 18 is an image of fluorescence $L_F$ generated in the vicinity of a plane in the observation object 90 (this plane will be referred to hereinafter as "fluorescence observation plane"), the image being focused on the imaging screen of the fluorescence imaging unit 18 by the focusing optical system (the objective lens 16 and the lens 14) located between the observation object 90 and the fluorescence imaging unit 18. On the other hand, the interference image acquired by the interference imaging unit 29 is an image of reflection of the position detection light $L_Z$ generated in the vicinity of a plane in the observation object 90 (this plane will be referred to hereinafter as "interference observation plane") where the difference between the respective optical path lengths of the first optical path and the second optical path is 0.

Figure 6:
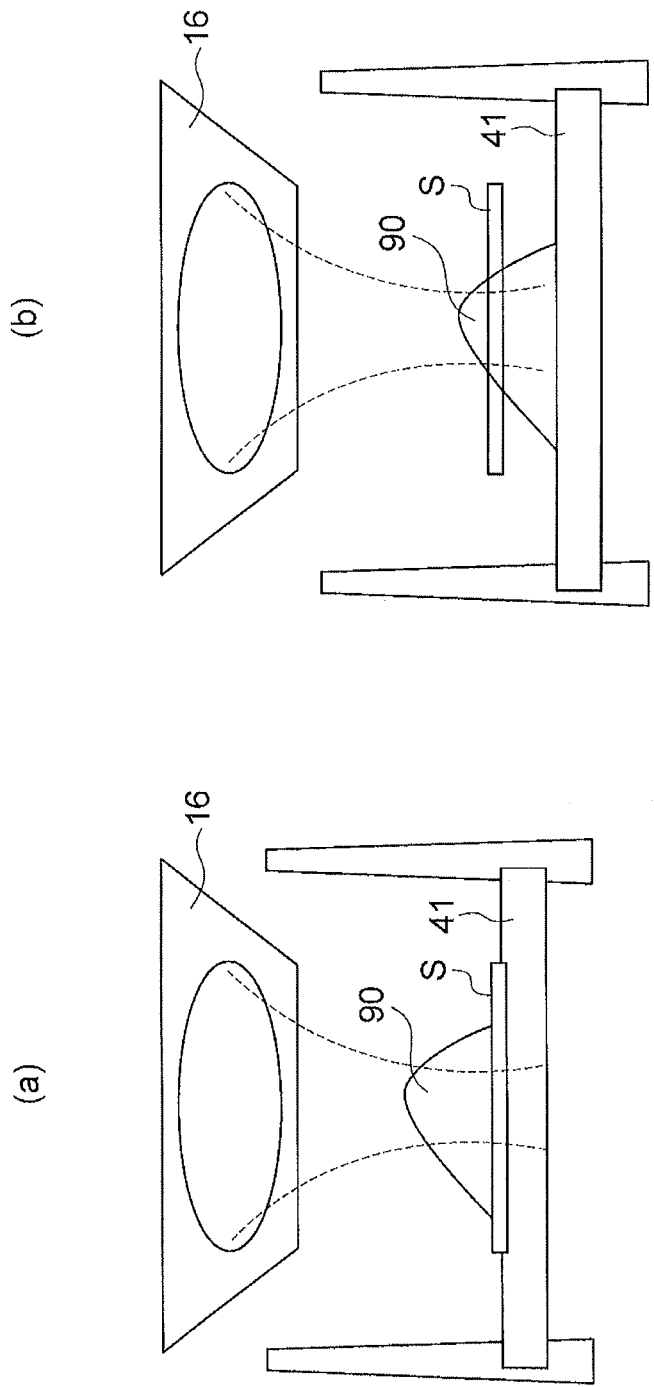
FIG. 6 is a drawing showing arrangement relations between the objective lens 16 and the slide glass 41.

FIG. 6 is a drawing showing arrangement relations between the objective lens 16 and the slide glass 41. When the fluorescence observation plane and the interference observation plane are set as a common observation plane S, we can acquire the fluorescence image and the interference image on the common observation plane in the observation object 90 substantially at the same time. In Part (a) of FIG. 6, the common observation plane S is set on the top face of the slide glass 41. In Part (b) of FIG. 6, the slide glass 41 is moved down by the actuator 42 with respect to Part (a) of FIG. 6, whereby the common observation plane S is set in the observation object 90. The slide glass 41 is moved by the actuator 42 while monitoring and feedback-controlling the position of the slide glass 41 by the position detection light source 31 and the light detection unit 32, whereby the fluorescence image and interference image can be acquired substantially at the same time on any desired observation plane in the observation object 90.

For setting the fluorescence observation plane and the interference observation plane as the common observation plane, the imaging operation by the fluorescence imaging unit 18 and the imaging operation by the interference imaging unit 29 are made to be carried out using an object of a known shape (e.g., a fluorescent bead) as a standard object, at each of a plurality of target positions of the slide glass 41 to acquire a three-dimensional fluorescence image and a three-dimensional interference image of the standard object. If there is a difference in relative position in the optical-axis direction between these three-dimensional fluorescence image and three-dimensional interference image, the fluorescence imaging unit 18 is moved in the optical-axis direction, or, a lens which can be moved independently of the focusing condition of the interference image, out of the lenses for focusing the fluorescence image, is moved in the optical-axis direction, whereby the optical system is finely adjusted so as to eliminate the difference in relative position between the three-dimensional fluorescence image and the three-dimensional interference image.

Figure 7:
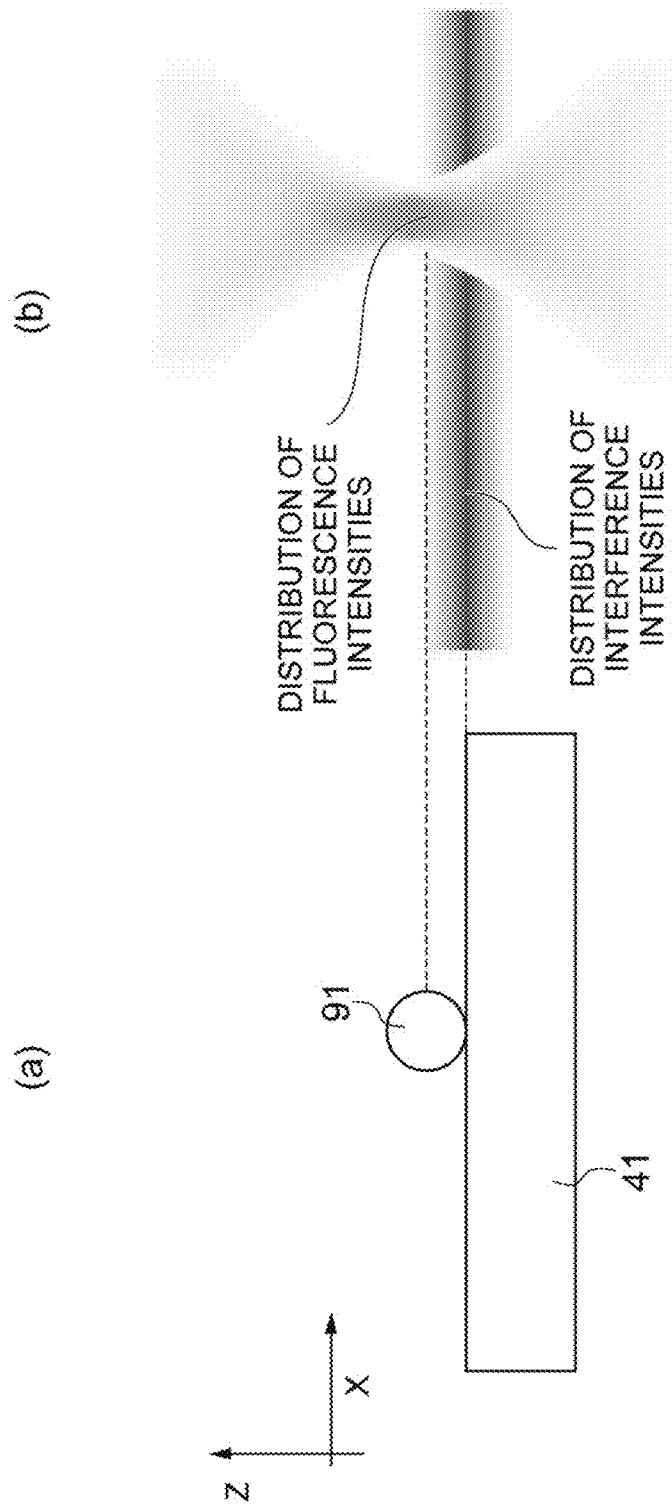
FIG. 7 is a drawing for explaining a method for setting a fluorescence observation plane and an interference observation plane as a common observation plane S.

FIG. 7 is a drawing for explaining a method for setting the fluorescence observation plane and the interference observation plane as the common observation plane S. A fluorescent bead 91 with a known radius is mounted on the slide glass 41 as shown in Part (a) of FIG. 7; fluorescence images are acquired by the fluorescence imaging unit 18 and interference images are acquired by the interference imaging unit 29 while vertically moving the slide glass 41 by the actuator 42; whereby respective Z-directional intensity distributions of the fluorescence images and the interference images are obtained as shown in Part (b) of FIG. 7. Such a fluorescent bead with the radius having an error of less than 1% is commercially available as a product on the market.

The Z-directional intensity distribution of the fluorescence images obtained in this manner has a maximum at the position of the center of the fluorescent bead 91. Furthermore, the Z-directional intensity distribution of the interference images has a maximum at the position of the top face of the slide glass 41. The position of the center of the fluorescent bead 91 is located up by the distance equal to the radius of the fluorescent bead 91 with respect to the position of the top face of the slide glass 41. Therefore, when the position of the maximum fluorescence intensity is located up by the distance equal to the radius of the fluorescent bead 91 from the position of the maximum interference intensity, we can determine that the fluorescence observation plane and the interference observation plane are set to be the common observation plane.

For setting the fluorescence observation plane and the interference observation plane as the common observation plane, the position in the optical-axis direction of the fluorescence imaging unit 18 or the interference imaging unit 29 is adjusted or the position in the optical-axis direction of the reference mirror 43 is adjusted so that the position of the maximum fluorescence intensity is located up by the distance equal to the radius of the fluorescent bead 91 from the position of the maximum interference intensity. By performing the preliminary adjustment of the optical system as described above, the fluorescence image and the interference image on the common observation plane in the observation object 90 can be acquired substantially at the same time thereafter.

The following will describe a method for obtaining an interference intensity image and an interference phase image based on interference images acquired by the interference imaging unit 29 and also describe a method for acquiring a fluorescence image, an interference intensity image, and an interference phase image on a common observation plane in the observation object 90 substantially at the same time. An interference image includes intensity information and phase information, an interference intensity image is an image indicative of the intensity information of the interference image, and an interference phase image is an image indicative of the phase information of the interference image.

The phase shift method is used to obtain the interference intensity image and the interference phase image (cf. Non Patent Literature 2). Specifically, the reference mirror 43 is moved by steps of a quarter of the wavelength $\lambda_I$ of the interference imaging light by the actuator 44 to acquire a set $P_M$ of four interference images and the set $P_M$ of these four interference images are subjected to arithmetic processing, whereby we can obtain the interference intensity image and the interference phase image. Alternatively, it is also possible to move the slide glass 41 and the observation object 90 by steps of a quarter of the wavelength $\lambda_I$ by the actuator 42.

Figure 8:
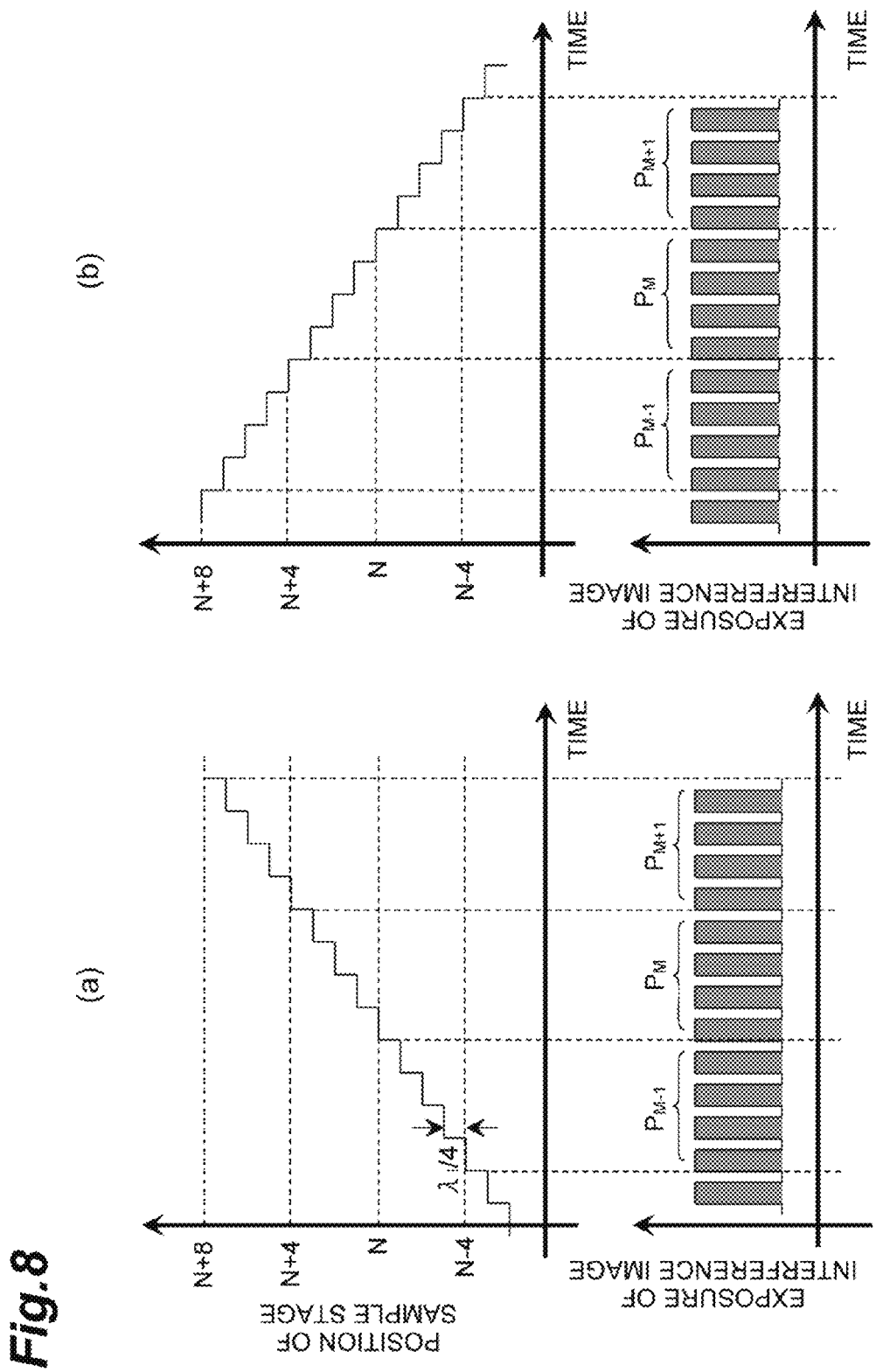
FIG. 8 is a drawing for explaining acquisition timing of each of interference images, interference intensity images, and interference phase images acquired by an interference imaging unit 29.

FIG. 8 is a drawing for explaining acquisition timing of each of interference images, interference intensity images, and interference phase images obtained by the interference imaging unit 29. As shown in Part (a) of FIG. 8, while the reference mirror 43 or the slide glass 41 is raised stepwise by steps of a quarter of the wavelength $\lambda_I$, interference images are acquired at the respective steps; the interference images are grouped into sets of four images and, four interference images in each set are subjected to arithmetic processing, thereby to obtain an interference intensity image and an interference phase image. In another example, as shown in Part (b) of FIG. 8, while the reference mirror 43 or the slide glass 41 is lowered stepwise by steps of a quarter of the wavelength $\lambda_I$, interference images are acquired at the respective steps; the interference images are grouped into sets of four images and, four interference images in each set are subjected to arithmetic processing, thereby to obtain an interference intensity image and an interference phase image. The interference intensity image and the interference phase image thus obtained are substantially those on the observation plane located at a middle position between the interference observation plane of the second interference image and the interference observation plane of the third interference image out of the four interference images in each set.

Figure 9:
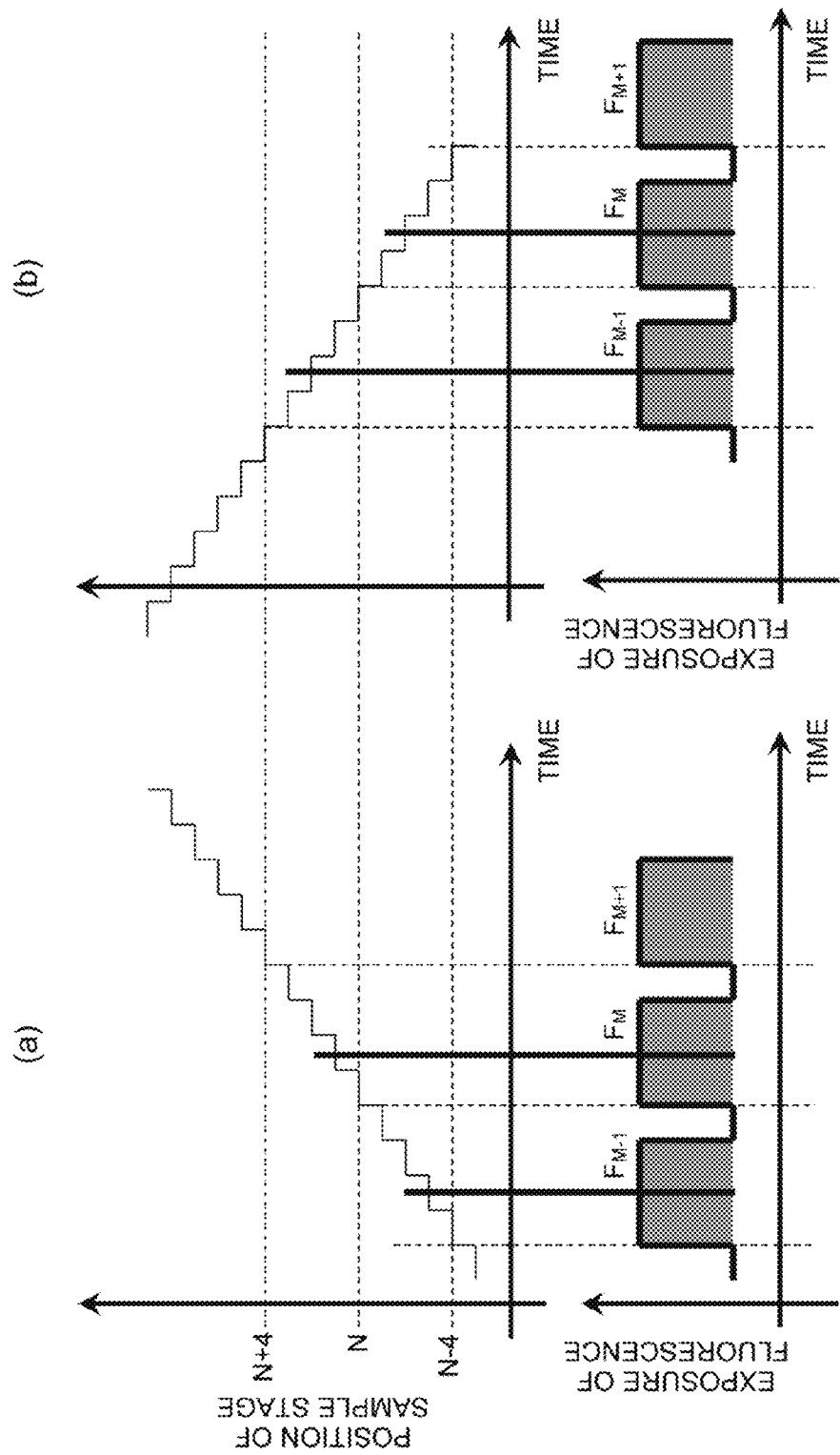
FIG. 9 is a drawing for explaining acquisition timing of fluorescence images acquired by a fluorescence imaging unit 18.

FIG. 9 is a drawing for explaining acquisition timing of fluorescence images obtained by the fluorescence imaging unit 18. Ideally, fluorescence images are acquired in synchronism with exposure of individual interference images and an average fluorescence image is created from four fluorescence images in the same manner as the acquisition of the interference intensity image and the interference phase image from four interference images, whereby these average fluorescence image, interference intensity image, and interference phase image can be those observed on a common observation plane. However, respective optimal exposure durations for the fluorescence image and for the interference image are different depending upon difference of light quantity or difference of sensitivities of the imaging units; for example, we can have such a situation that the exposure duration of the interference image is 100 msec whereas the exposure duration of the fluorescence image is 350 msec. For this reason, it is difficult to acquire fluorescence images in synchronism with exposures of individual interference images.

It is conceivable, as shown in FIG. 9, to start imaging of fluorescence image $F_M$ by the fluorescence imaging unit 18 with respect to each movement of four steps while the reference mirror 43 or the slide glass 41 is raised or lowered stepwise by steps of a quarter of the wavelength $\lambda_I$. In this case, however, there is difference in imaging timing of fluorescence image $F_M$ between the stepwise raising case (Part (a) of FIG. 9) and lowering case (Part (b) of FIG. 9) of the reference mirror 43 or the slide glass 41 by steps of a quarter of the wavelength $\lambda_I$. If a three-dimensional image of fluorescence images is attempted to make in the case where there is the difference in imaging timing between the raising occasion and the lowering occasion as described above, vertical deviation will arise between a tomographic view of fluorescence images created in the raising occasion and a tomographic view of fluorescence images created in the lowering occasion and false vibration will be observed, for example, in imaging of granules or the like.

Figure 10:
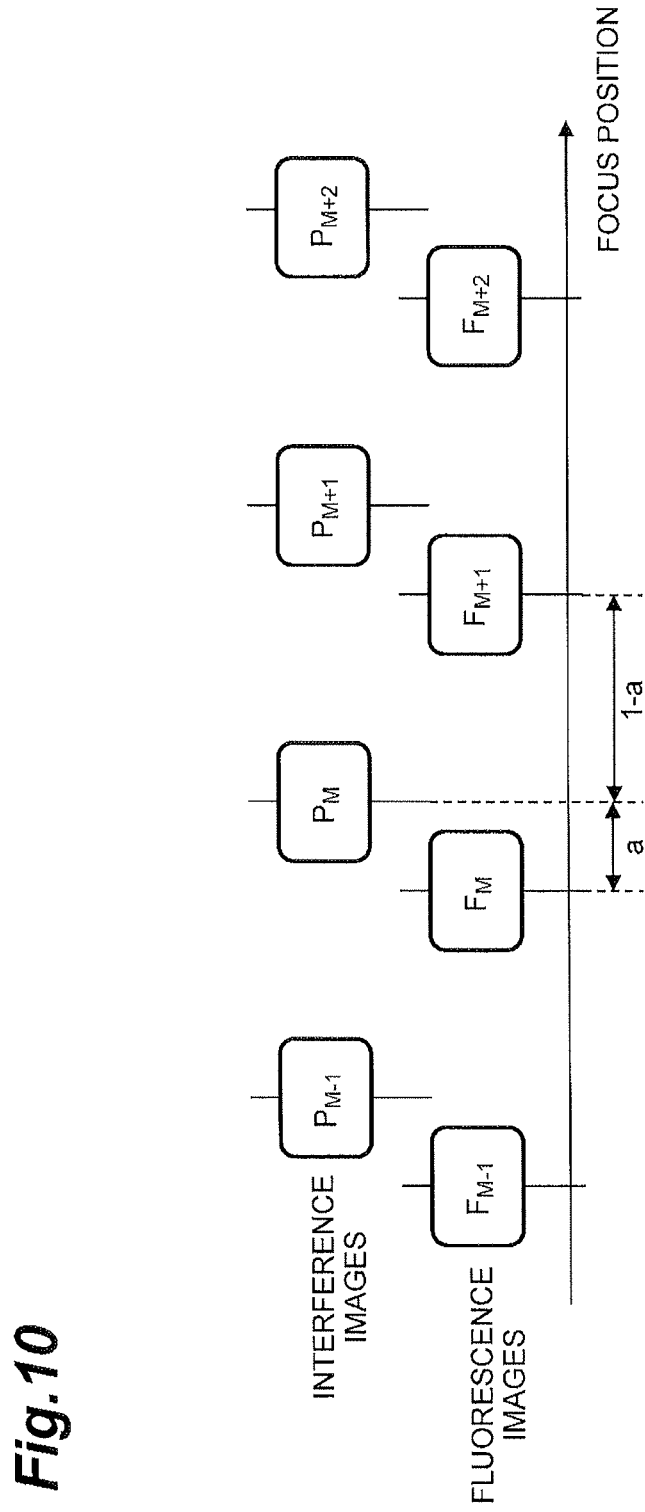
FIG. 10 is a drawing for explaining a method for obtaining a fluorescence image, an interference intensity image, and an interference phase image on a common observation plane in the observation object 90.

Then, the processing as shown in FIG. 10 can be carried out. FIG. 10 is a drawing for explaining a method for obtaining a fluorescence image, an interference intensity image, and an interference phase image on a common observation plane in the observation object 90. As shown in FIG. 10, adjustment of the observation plane is implemented by weight ratio averaging of images. In the case where there is deviation between respective observation planes of the fluorescence image and the interference intensity image•interference phase image due to the aforementioned problem, it is assumed that the observation plane of the interference intensity image•interference phase image obtained from a set $P_M$ of four interference images is a plane obtained by internally dividing the length between the observation plane of the fluorescence image $F_M$ and the observation plane of the fluorescence image $F_{M+1}$ at the ratio of a:(1−a). At this time, when $(1-a)F_{M+a}F_{M+1}$ is used as a true fluorescence image $F_M$, we can obtain the fluorescence image, the interference intensity image, and the interference phase image on a common observation plane in the observation object 90.

With use of the observation device of the present embodiment, as described above, the distance between the observation plane under imaging and the reference plane such as the surface of the slide glass can be determined with high accuracy in acquiring the fluorescence image and the interference image of the observation object, and thus the fluorescence image and the interference image generated on the observation plane at a desired position can be acquired with certainty. Furthermore, since it becomes feasible to acquire the fluorescence image and the interference image generated on the observation plane at a desired position, we can also obtain three-dimensional fluorescence and interference images. This effect is also useful further for estimating a distribution of fluorochrome in high resolution by a numerical analysis such as deconvolution.

With use of the observation device of the present embodiment, we can acquire the fluorescence image and the interference image on the common observation plane in the observation object substantially at the same time. This allows us, for example, in the case of the observation object of a cell, to obtain chemical physiological information of the observation object from the fluorescence image and, at the same time as it, it allows us to obtain the morphological information of the observation object from the interference image, whereby we can find out properties of the observation object in more detail.

When a granular object inside the observation object 90 is fluorescently stained and a plurality of three-dimensional fluorescence images and three-dimensional interference images of the observation object 90 are taken in time series, it is possible to visualize a relative positional relation between the fluorescently-stained granular object and a film-like structure on the surface or inside of the observation object 90.

Particularly, use of the interference phase image allows us to highly accurately observe the morphology of the film-like structure in the observation object. A conceivable application is, for example, such that in a cell sample a fluorochrome is clearly determined to be present inside or outside a cell membrane or a nuclear membrane and movement of the fluorochrome inside the cell is three-dimensionally tracked.

Another application example is such that, at a start of observation, the irradiation with the excitation light by the excitation light source 11 is carried out and the imaging operation by the fluorescence imaging unit 18 and the imaging operation by the interference imaging unit 29 are carried out, only for a duration of time shorter than an overall time duration of observation; correspondence is made between a fluorescently-labeled object and an object resulting from feature extraction by interference imaging from images obtained by the operations. Then, after completion of the imaging at the start of observation, the irradiation with the excitation light by the excitation light source 11 is not carried out, and only the imaging operation by the interference imaging unit 29 is carried out, whereby the fluorescently-labeled object can be observed with a lapse of time. This allows us to perform the temporal observation of the fluorescently-labeled object without being affected by photo-bleaching.

The below will describe Examples 1 to 3 using the observation device of the present embodiment and show the fluorescence images, interference intensity images, and interference phase images acquired in each of Examples.

EXAMPLE 1

In Example 1, a fluorescent bead 91 with the diameter of 20 μm (FP-20052-5 manufactured by SPHERO TECH) was mounted on the slide glass 41 and interference intensity images, interference phase images, and fluorescence images thereof were acquired. In Example 1, fluorescence images and interference images on the observation plane S at respective positions were acquired and stacked and a three-dimensional fluorescence image and a three-dimensional interference image of the fluorescent bead 91 were acquired based on these images.

Figure 11:
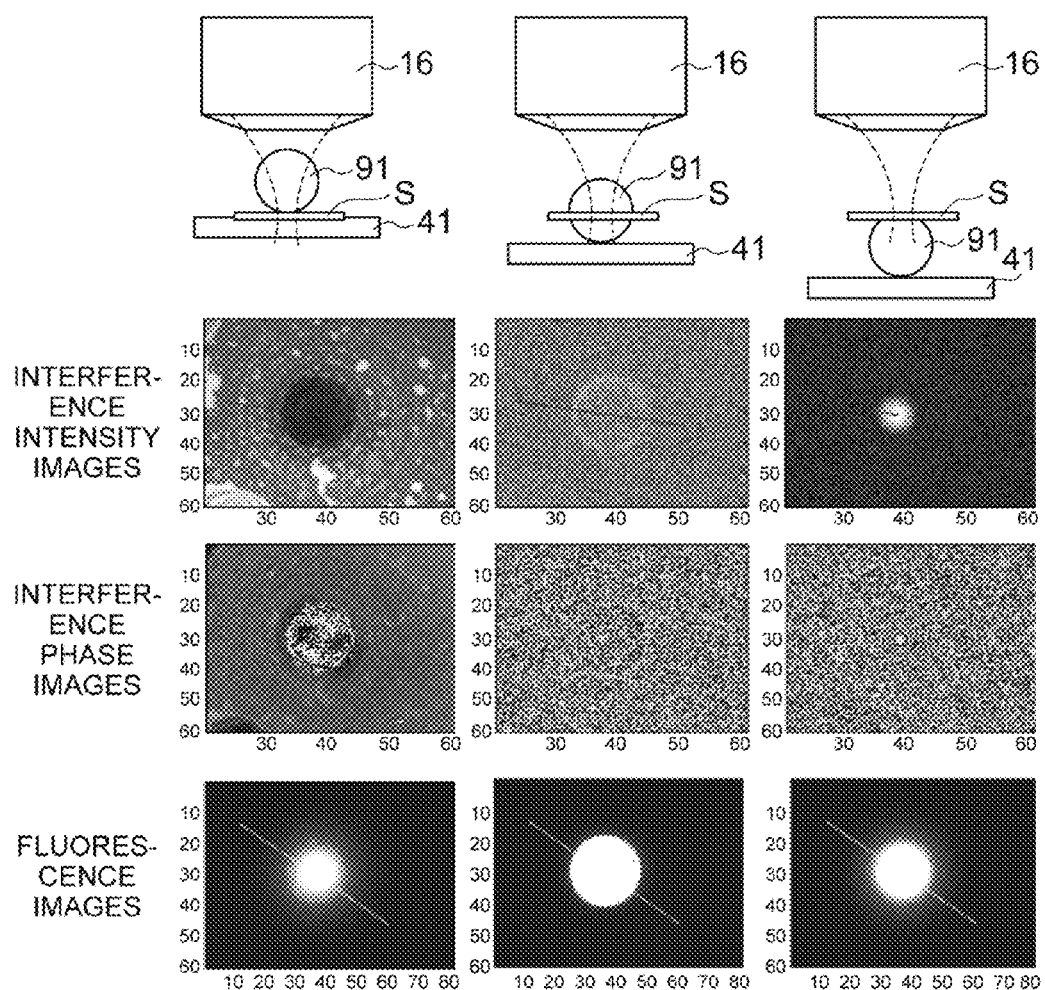
FIG. 11 is a drawing showing interference intensity images, interference phase images, and fluorescence images acquired on the observation plane S at respective positions in Example 1.

FIG. 11 is a drawing showing the interference intensity images, interference phase images, and fluorescence images acquired on the observation plane S at respective positions in Example 1. In FIG. 11, the topmost row shows the positions of the observation plane S in the fluorescent bead 91, the second row the interference intensity images, the third row the interference phase images, and the lowermost row the fluorescence images. The leftmost column shows the case where the observation plane S is located on the top face of the slide glass 41, the center column the case where the observation plane S is located near the central part of the fluorescent bead 91, and the rightmost column the case where the observation plane S is located near the top of the fluorescent bead 91. It is seen from FIG. 11 that the images according to the observation plane S at the respective positions were acquired. In acquisition of these images, scanning across 29 μm up and down was conducted so as to cover the whole of the diameter 20 μm of the fluorescent bead 91 and repetitions of this scanning found that the same images were obtained as to all of the interference intensity image, the interference phase image, and the fluorescence image on the observation plane S at the same position.

Figure 12:
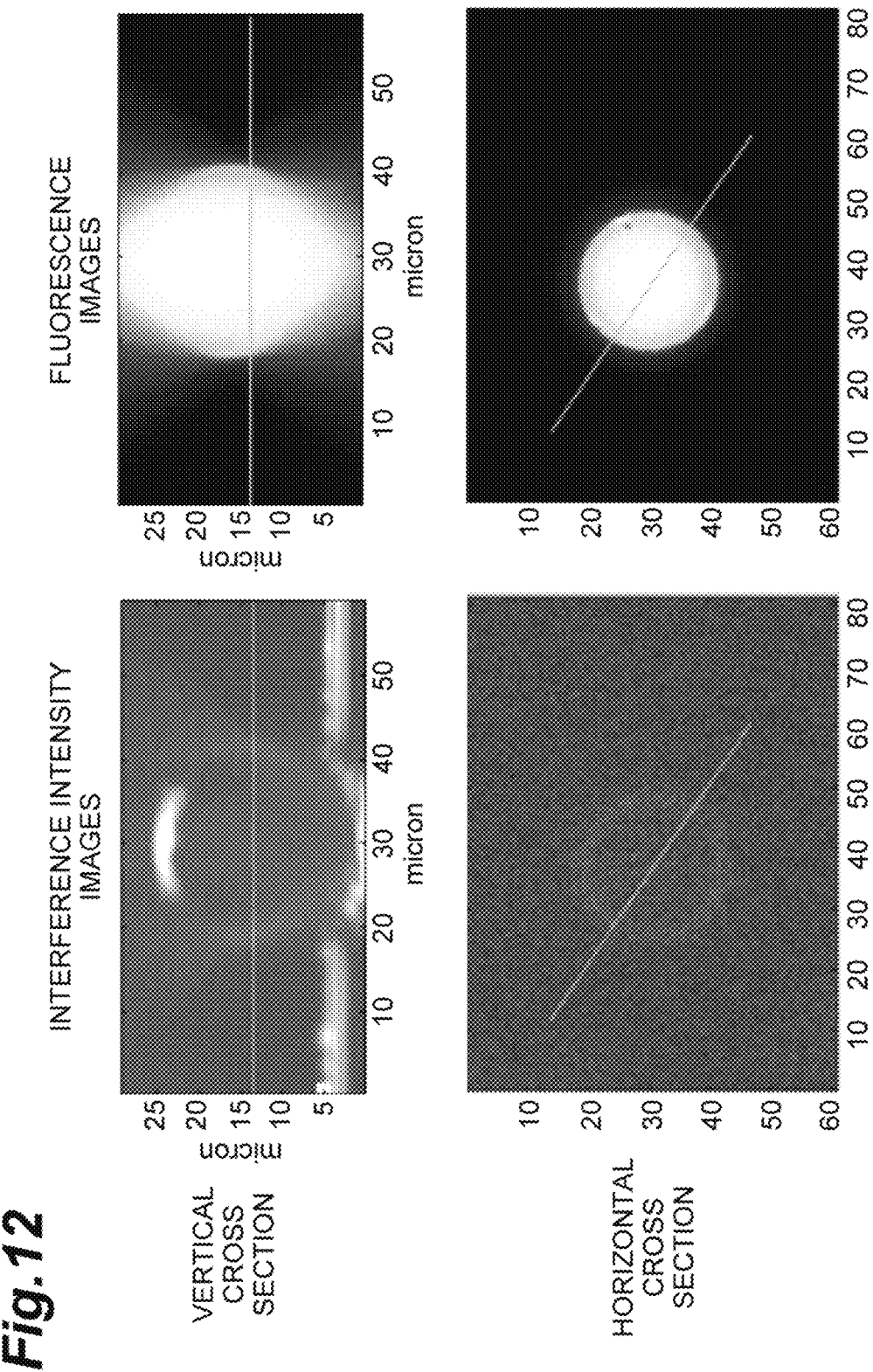
FIG. 12 is a drawing showing interference intensity images and fluorescence images in a vertical cross section and in a horizontal cross section acquired in Example 1.

FIG. 12 is a drawing showing the interference intensity images and the fluorescence images in the vertical cross section and in the horizontal cross section acquired in Example 1. In FIG. 12, the upper row shows the images in the vertical cross section and the lower row the images in the horizontal cross section. The left column shows the interference intensity images and the right column the fluorescence images. Each straight line in the drawing indicates the cut position of the horizontal cross section in the vertical cross section or the cut position of the vertical cross section in the horizontal cross section.

EXAMPLE 2

In Example 2, the observation object 90 used was a uterine-cervix-cancer-derived cultured cell HeLa and a fluorochrome used for dyeing the lipid membrane of this cell was DiO. The absorption peak wavelength of this fluorochrome is 484 nm and the emission peak wavelength 501 nm.

Figure 13:
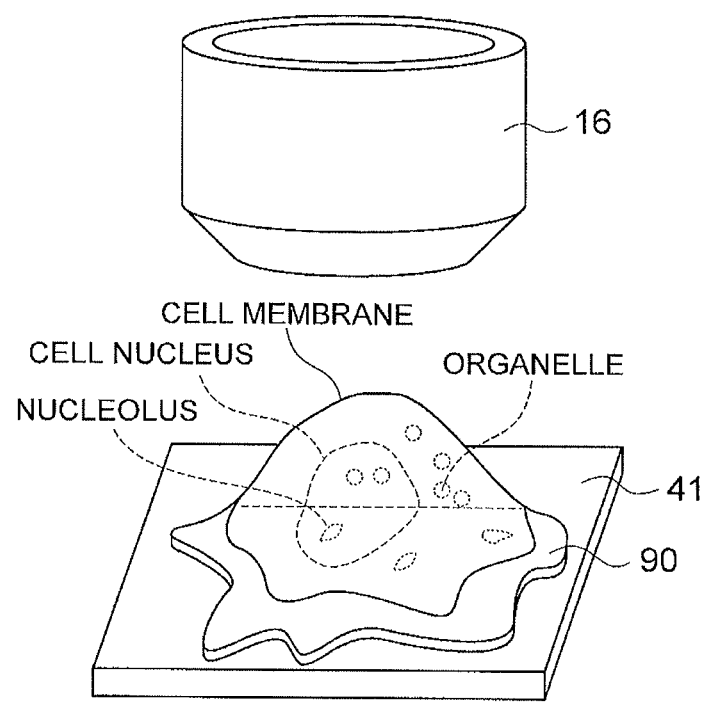
FIG. 13 is a drawing schematically showing a structure of a cell used as observation object 90 in Example 2.

FIG. 13 is a drawing schematically showing the structure of the cell used as observation object 90 in Example 2. When the observation plane is set at any desired position, various structural objects in the cell can be observed on the observation plane.

Figure 14:
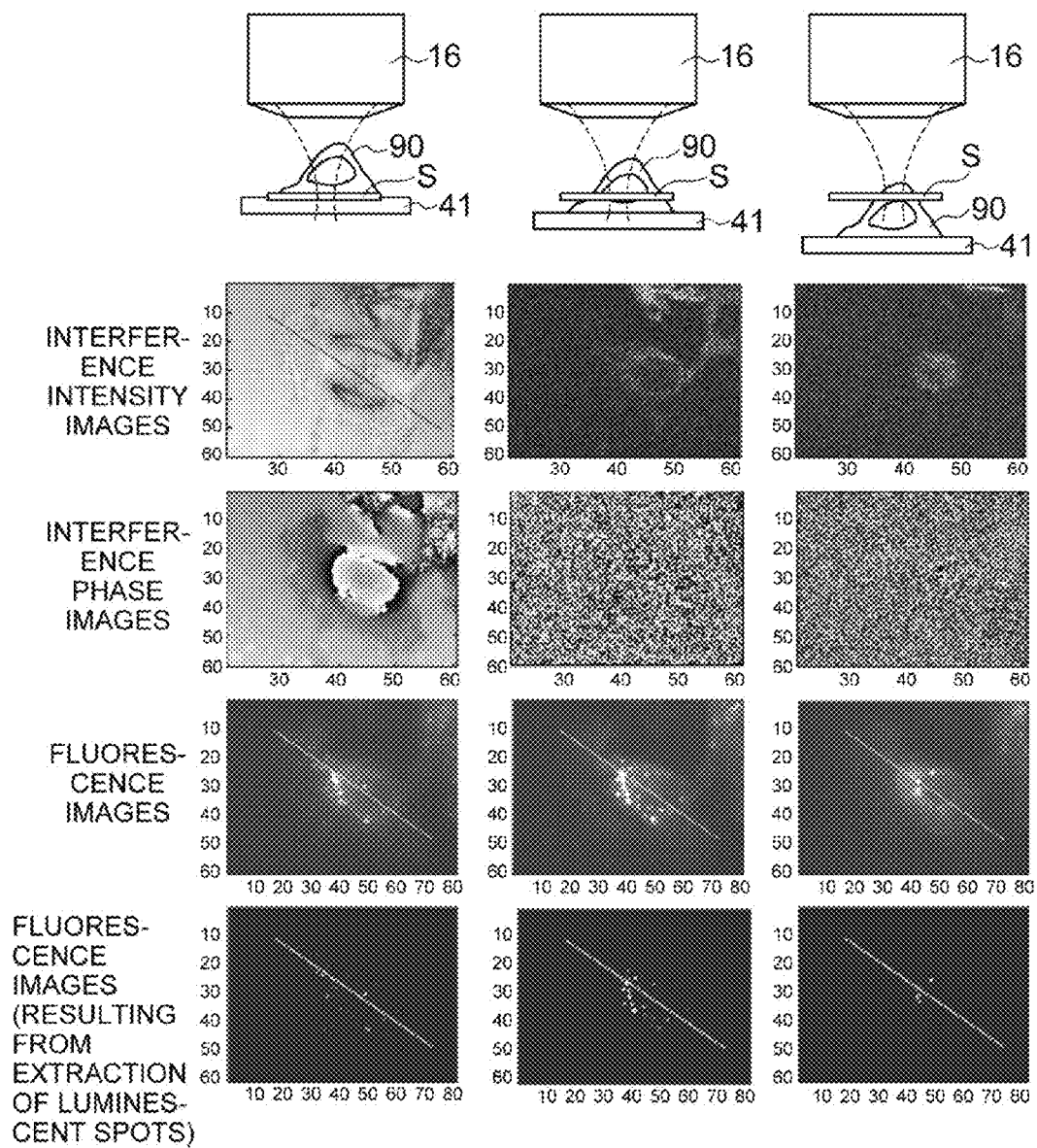
FIG. 14 is a drawing showing interference intensity images, interference phase images, and fluorescence images acquired on the observation plane S at respective positions in Example 2.

FIG. 14 is a drawing showing the interference intensity images, interference phase images, and fluorescence images acquired on the observation plane S at respective positions in Example 2. In FIG. 14, the topmost row shows the positions of the observation plane S in the observation object 90, the second row the interference intensity images, the third row the interference phase images, the fourth row the fluorescence images, and the lowermost row images obtained by extracting luminescent spots from the fluorescence images. The leftmost column shows the case where the observation plane S is located on the top face of the slide glass 41, the center column the case where the observation plane S is located near the central part of the observation object 90, and the rightmost column the case where the observation plane S is located near the top of the observation object 90.

Figure 15:
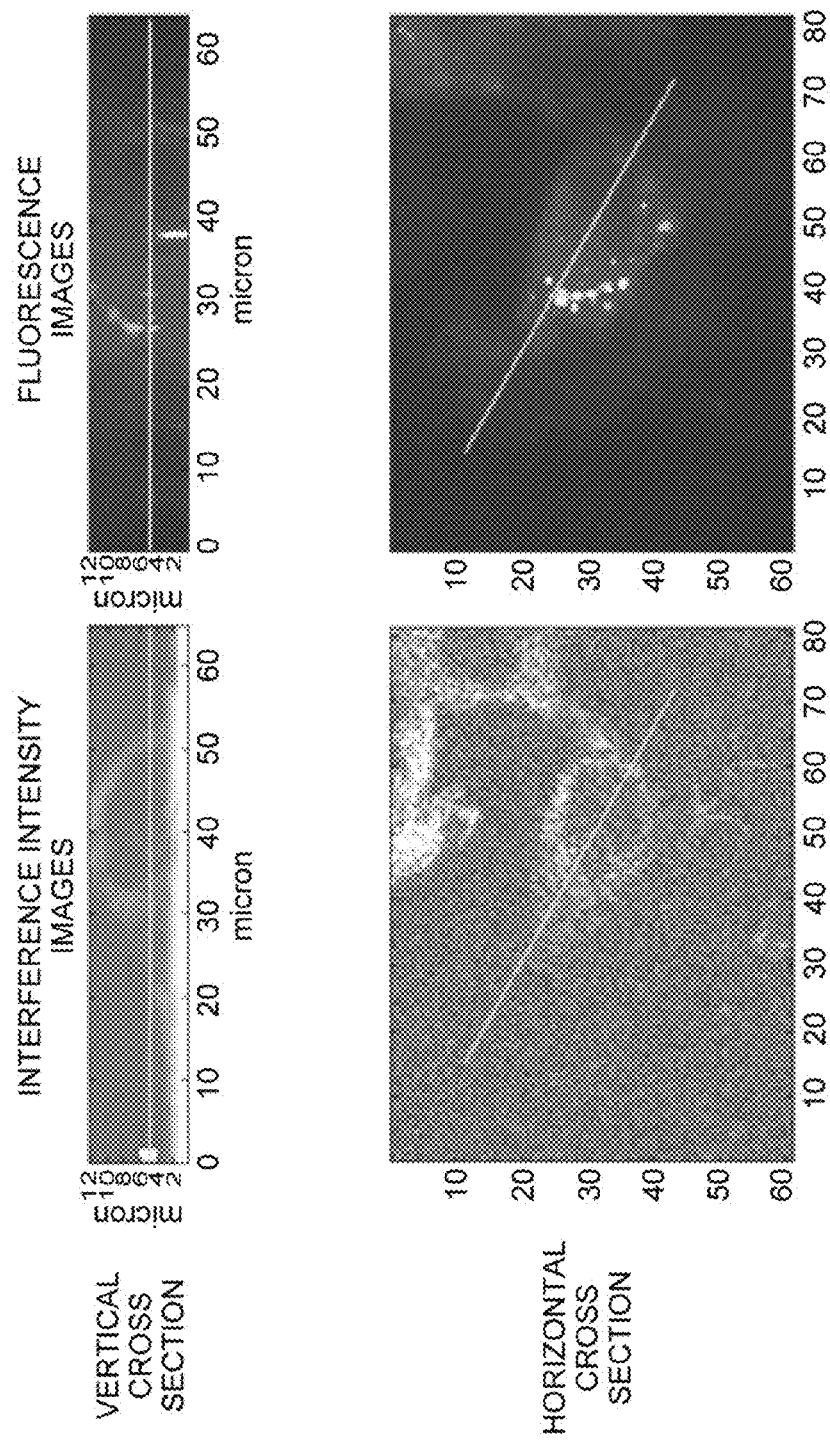
FIG. 15 is a drawing showing interference intensity images and fluorescence images in the vertical cross section and in the horizontal cross section acquired in Example 2.

FIG. 15 is a drawing showing the interference intensity images and the fluorescence images in the vertical cross section and in the horizontal cross section acquired in Example 2. In FIG. 15, the upper row shows the images in the vertical cross section and the lower row the images in the horizontal cross section. The left column shows the interference intensity images and the right column the fluorescence images.

It is seen from these drawings that the morphological information of the cell can be obtained from the interference images (interference intensity images•interference phase images) and, at the same time as it, the physiological information in the cell (distribution of the lipid membrane) can be obtained from the fluorescence images.

EXAMPLE 3

Figure 16:
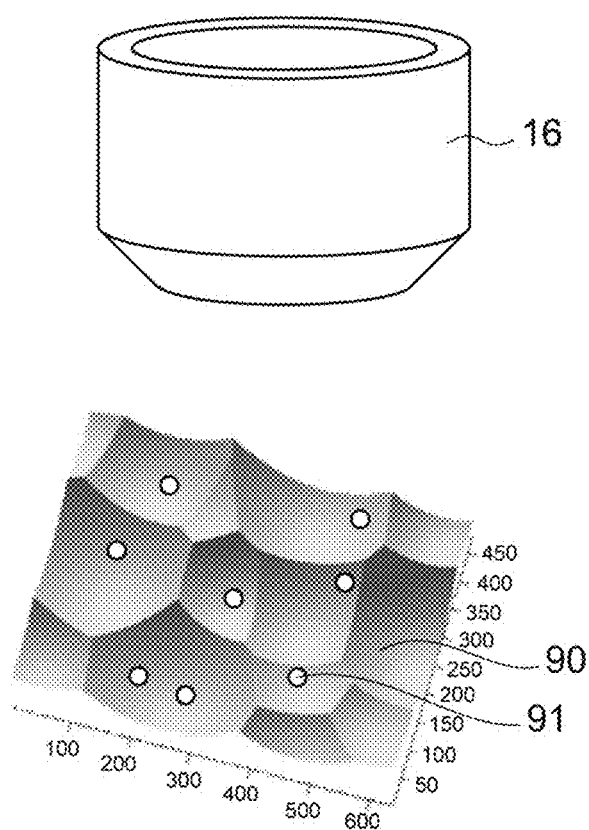
FIG. 16 is a drawing showing a configuration of a sample used as observation object 90 in Example 3.

In Example 3, as shown in FIG. 16, the observation object 90 used was a glass substrate with the uneven surface of several μm etched with a chemical and a sample was prepared by scattering fluorescent beads 91 with the diameter of 2.5 μm over the uneven surface. Since the surface of the glass substrate was uneven, there was variation of heights of the fluorescent beads 91 as well. The interference intensity image, interference phase image, and fluorescence image were acquired on the observation plane set at each of positions and phase unwrapping was effected based on the interference phase images at the respective positions to obtain the uneven shape of the surface of the observation object 90.

Figure 17:
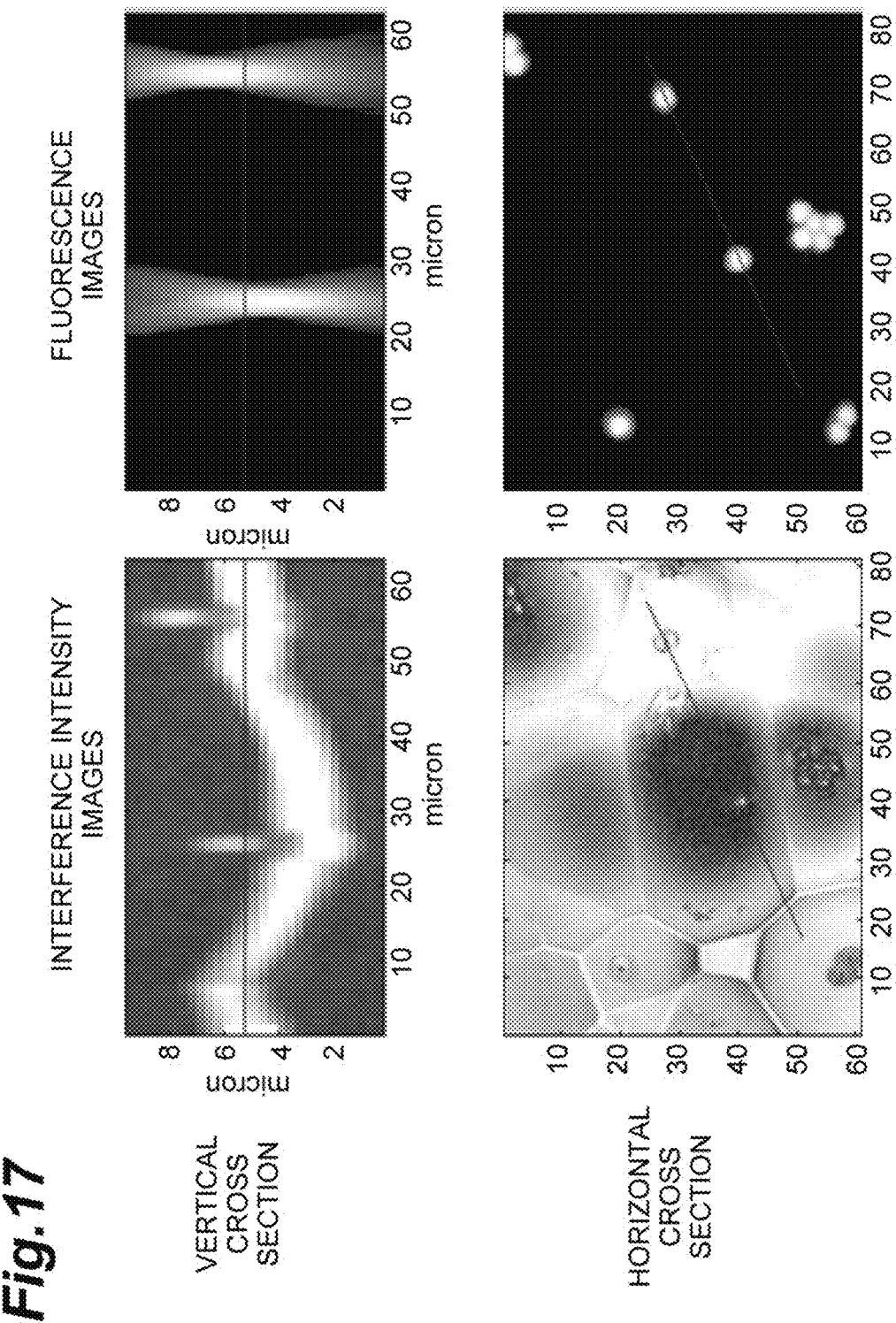
FIG. 17 is a drawing showing interference intensity images and fluorescence images in the vertical cross section and in the horizontal cross section acquired in Example 3.

FIG. 17 is a drawing showing the interference intensity images and the fluorescence images in the vertical cross section and in the horizontal cross section acquired in Example 3. In FIG. 17, the upper row shows the images in the vertical cross section and the lower row the images in the horizontal cross section. The left column shows the interference intensity images and the right column the fluorescence images.

Figure 18:
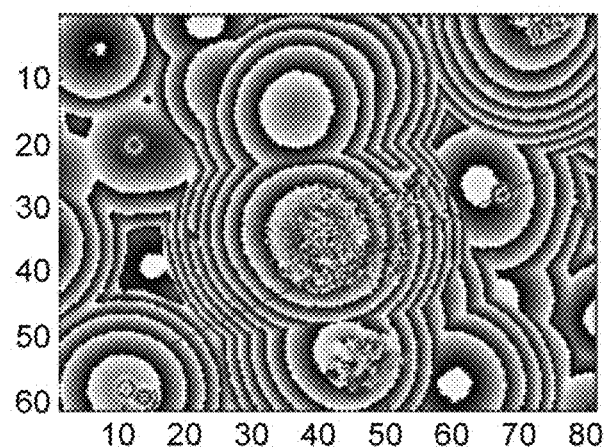
FIG. 18 is a drawing showing a phase image resulting from phase unwrapping based on interference phase images at respective positions in Example 3.

FIG. 18 is a drawing showing a phase image resulting from the phase unwrapping based on the interference phase images at the respective positions in Example 3. Since the surface of the glass substrate as observation object 90 has smoothly-varying unevenness, clear contours of phases were obtained as the result of the phase unwrapping.

Figure 19:
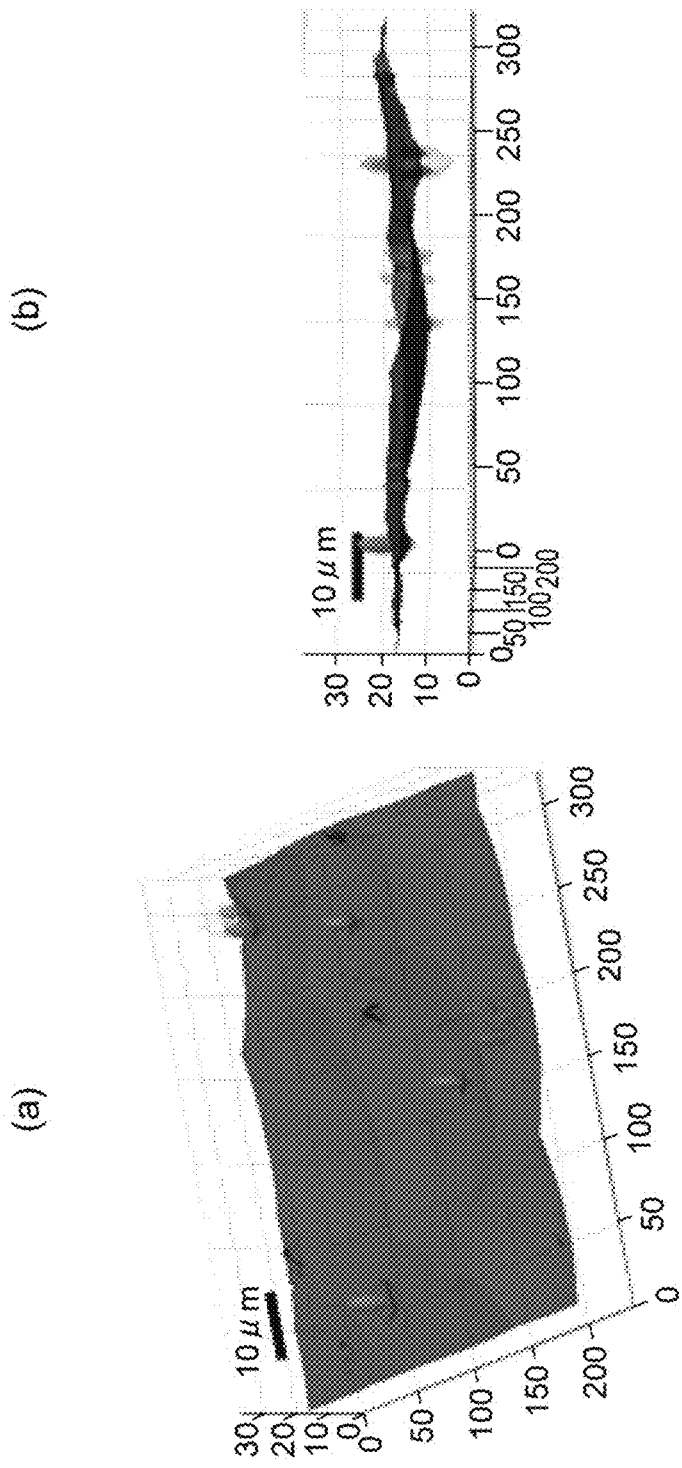
FIG. 19 is a drawing in which three-dimensional data of fluorescence intensities of fluorescent beads 91 is superimposed on a surface geometry of the observation object 90 obtained by phase unwrapping in Example 3, by volume rendering.

FIG. 19 is a drawing obtained by superimposing three-dimensional data of fluorescence intensities of the fluorescent beads 91 on the surface shape of the observation object 90 acquired by the phase unwrapping in Example 3, by volume rendering. As shown in FIG. 19, it becomes feasible to simultaneously display the surface shape of the observation object 90 and the three-dimensional distribution of fluorescence information of the fluorescent beads 91.

Figure 20:
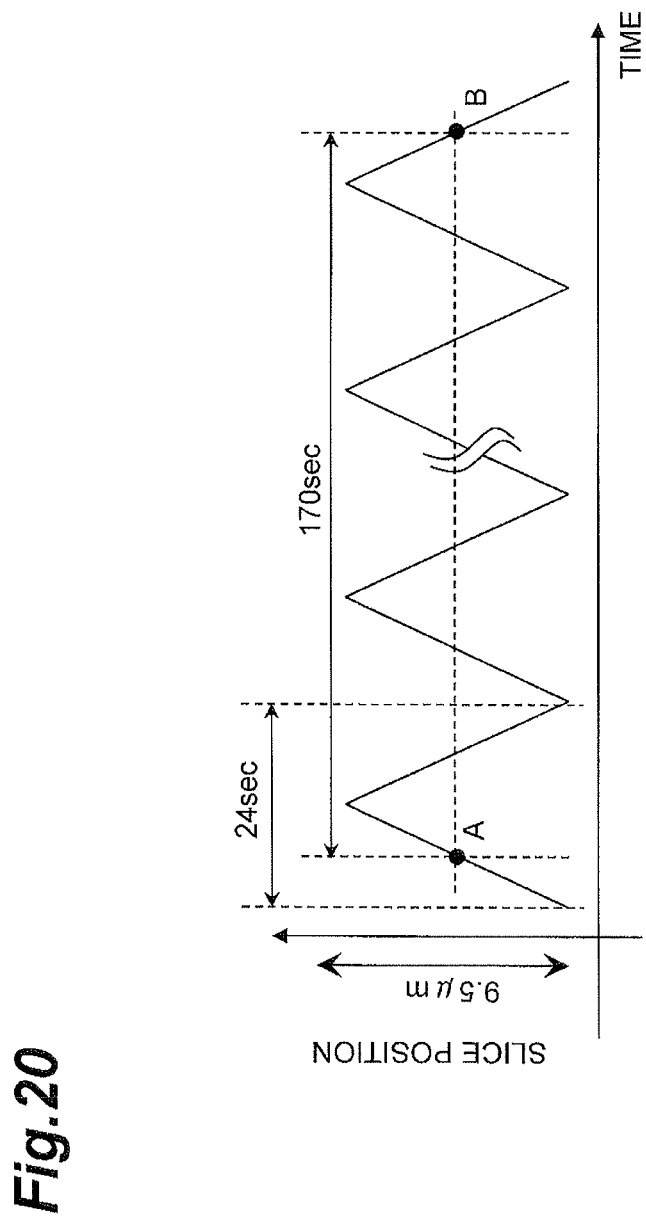
FIG. 20 is a drawing showing temporal change of position of the observation plane in Example 3.

In Example 3, as shown in FIG. 20, the observation plane was repeatedly moved up and down in the width of 9.5 μm to acquire the interference intensity images, interference phase images, and fluorescence images. The duration of time needed for one up and down movement was 24 seconds and the number of up and down movements was 16.

Figure 21:
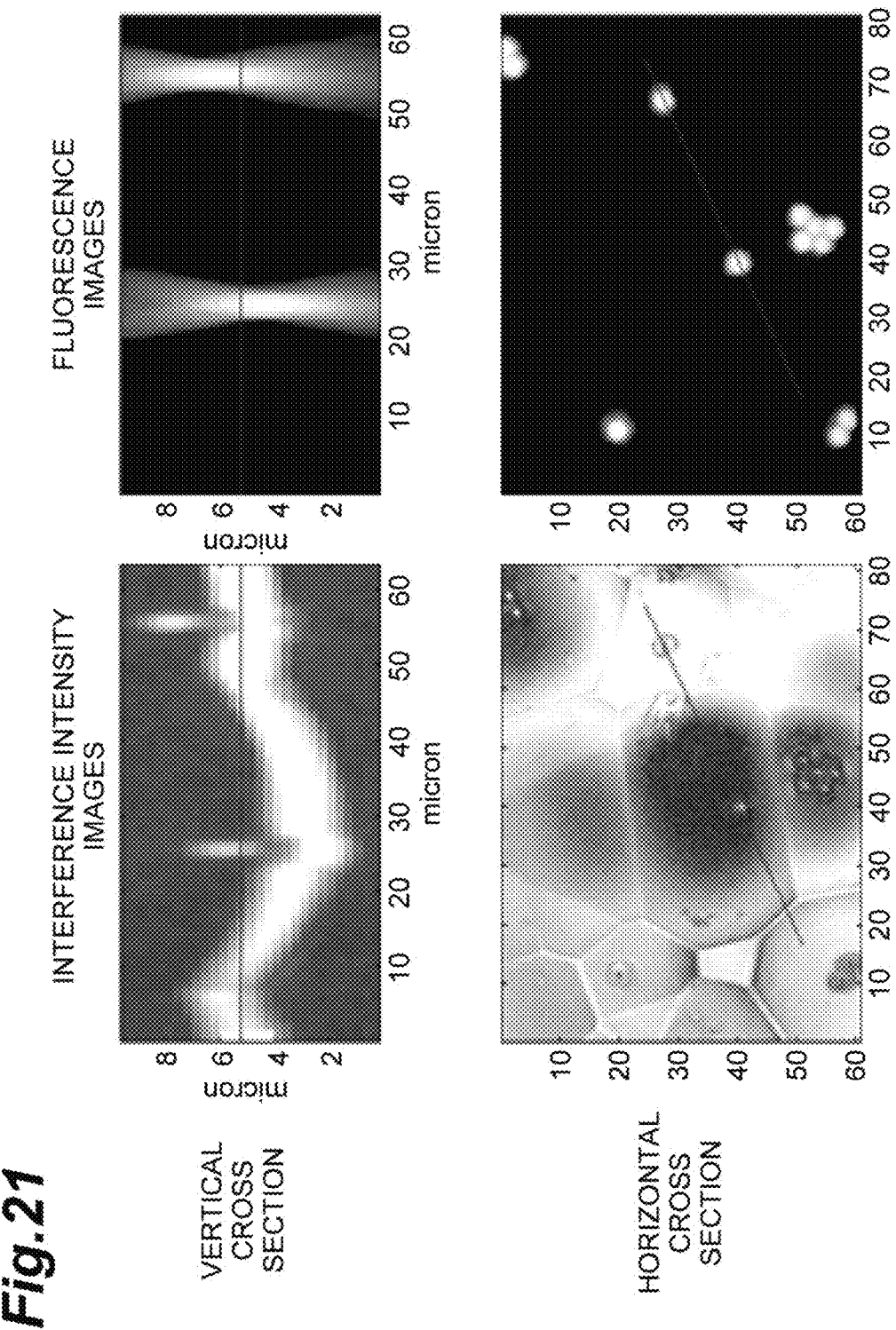
FIG. 21 is a drawing showing interference intensity images and fluorescence images in the vertical cross section and in the horizontal cross section acquired in Example 3.
Figure 22:
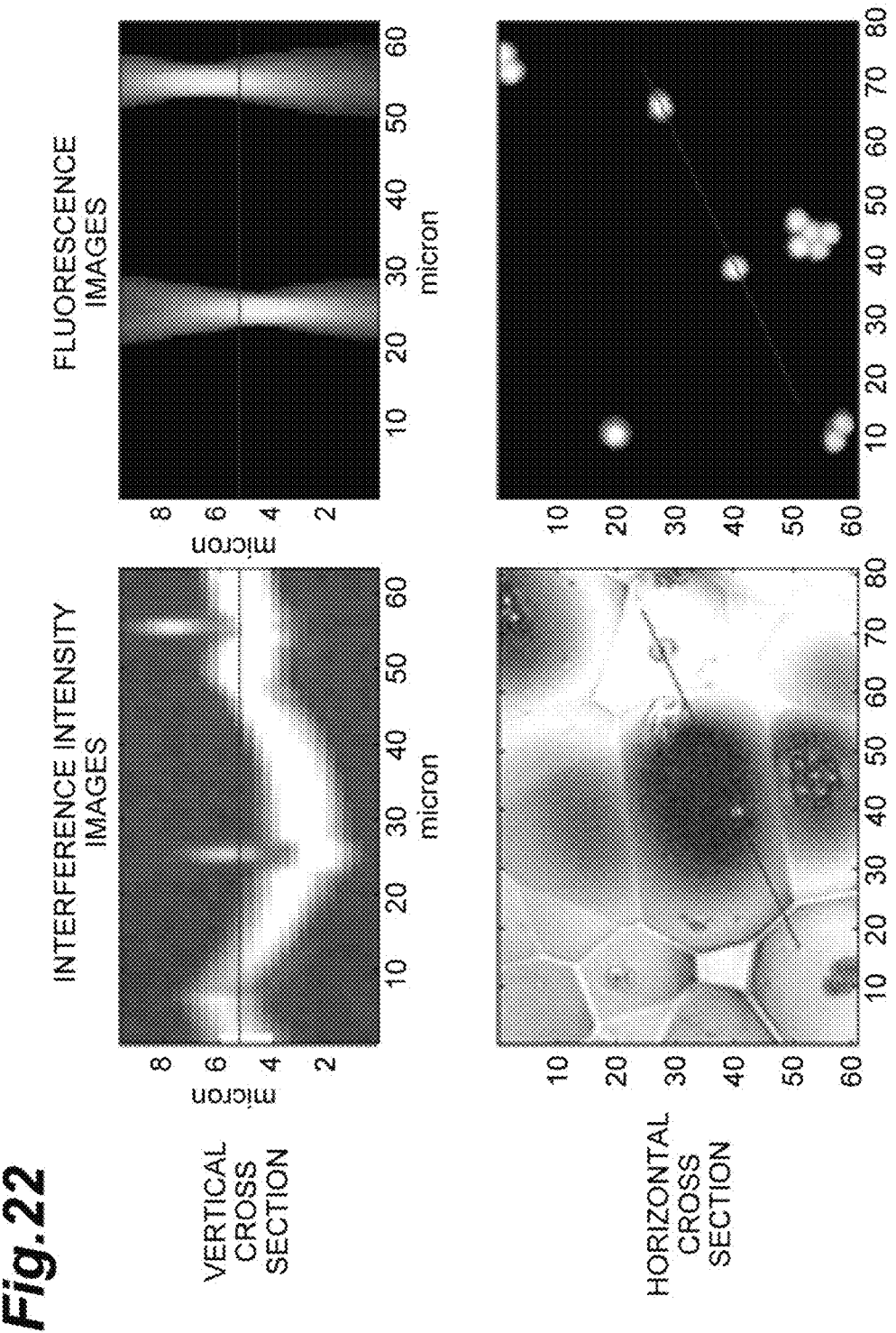
FIG. 22 is a drawing showing interference intensity images and fluorescence images in the vertical cross section and in the horizontal cross section acquired in Example 3.

FIG. 21 is a drawing showing the interference intensity images and the fluorescence images in the vertical cross section and in the horizontal cross section acquired at the position of height 5 μm (point A in FIG. 20) in the middle of upward movement of the observation plane in the first up and down movement. FIG. 22 is a drawing showing the interference intensity images and the fluorescence images in the vertical cross section and in the horizontal cross section acquired at the position of height 5 μm (point B in FIG. 20) in the middle of downward movement of the observation plane in the sixteenth up and down movement. In each of FIGS. 21 and 22, the upper row shows the images in the vertical cross section and the lower row the images in the horizontal cross section. The left column shows the interference intensity images and the right column the fluorescence images.

As seen from comparison between FIG. 21 and FIG. 22, both of the interference intensity images and the fluorescence images acquired in the respective cases can be said to appear identical beyond recognition even after the repetitive changes of the position of the observation plane as long as the observation plane is located at the same position.

INDUSTRIAL APPLICABILITY

The observation device according to the present embodiment is applicable to the technology for substantially simultaneously acquiring the fluorescence image and the interference image on the common observation plane in the observation object.

REFERENCE SIGNS LIST

1 . . . observation device; 11 . . . excitation light source; 12 . . . filter; 13 . . . dichroic mirror; 14 . . . lens; 15 . . . dichroic mirror; 16 . . . objective lens; 17 . . . filter; 18 . . . fluorescence imaging unit; 21 . . . interference imaging light source; 22 . . . filter; 23 . . . dichroic mirror; 24 . . . lens; 25 . . . half mirror; 26 . . . objective lens; 27 . . . lens; 28 . . . dichroic mirror; 29 . . . interference imaging unit; 31 . . . position detection light source; 32 . . . light detection unit; 41 . . . slide glass; 42 . . . actuator; 43 . . . reference mirror; 44 . . . actuator; 51 . . . control unit; 52 . . . display unit; 90 . . . observation object.

The invention claimed is:

1. An observation device comprising:

an excitation light source for outputting excitation light;

an objective lens for implementing irradiation of an observation object with the excitation light output from the excitation light source and receiving fluorescence generated in the observation object in accordance with the irradiation;

a fluorescence imaging unit for taking an image of the fluorescence generated in the observation object and guided through the objective lens;

a mount unit for the observation object to be mounted thereon, which is movable in an optical-axis direction of the objective lens;

an interference imaging light source for outputting interference imaging light;

a position detection light source for outputting position detection light;

a multiplexing unit for multiplexing the interference imaging light output from the interference imaging light source and the position detection light output from the position detection light source and outputting the light multiplexed;

an interference optical system for splitting the light multiplexed and output by the multiplexing unit, into two beams and outputting the two beams as a first branch beam and a second branch beam, for implementing application of the first branch beam through the objective lens onto the observation object or onto the mount unit and receiving input of first reflection generated in accordance with the application, for implementing application of the second branch beam onto a reference mirror and receiving input of second reflection generated in accordance with the application, and for letting the first reflection and the second reflection interfere with each other and outputting resultant light;

a demultiplexing unit for demultiplexing the light output from the interference optical system into the interference imaging light and the position detection light and outputting the interference imaging light and the position detection light;

an interference imaging unit for taking an interference image of the interference imaging light output from the demultiplexing unit;

a light detection unit for implementing detection of interference intensity of the position detection light output from the demultiplexing unit; and a control unit for acquiring the result of the detection by the light detection unit and for controlling a positioning operation of the mount unit, an imaging operation by the fluorescence imaging unit, and an imaging operation by the interference imaging unit, wherein the control unit performs as follows:

the control unit determines an optical path length difference between an optical path of the position detection light from the position detection light source via the mount unit to the light detection unit and an optical path of the position detection light from the position detection light source via the reference mirror to the light detection unit, based on the result of the detection of the interference intensity by the light detection unit;

the control unit performs feedback control based on the optical path length difference thus determined, thereby to set a position of the mount unit to a target position;

the control unit makes both or either one of the imaging operation by the fluorescence imaging unit and the imaging operation by the interference imaging unit carried out at the target position of the mount unit.

2. The observation device according to claim 1, wherein the position detection light output from the position detection light source is guided through the objective lens to be applied to a position on the mount unit where the observation object is absent.

3. The observation device according to claim 1, wherein the control unit makes the imaging operation by the fluorescence imaging unit or the imaging operation by the interference imaging unit carried out at each of a plurality of target positions of the mount unit to acquire two-dimensional fluorescence images or two-dimensional interference images, and acquires a three-dimensional fluorescence image or a three-dimensional interference image of the observation object, based on the images.

4. The observation device according to claim 1, wherein the control unit obtains an interference intensity image or an interference phase image, based on the interference image taken by the interference imaging unit.

5. The observation device according to claim 1, further comprising a display unit for displaying the fluorescence image taken by the fluorescence imaging unit and the interference image taken by the interference imaging unit.

6. The observation device according to claim 1, wherein the control unit makes the imaging operation by the fluorescence imaging unit and the imaging operation by the interference imaging unit carried out at each of a plurality of target positions of the mount unit to acquire two-dimensional fluorescence images and two-dimensional interference images in synchronism, and acquires a three-dimensional fluorescence image and a three-dimensional interference image of the observation object, based on the images.

7. The observation device according to claim 6, wherein at each of a plurality of target positions of the mount unit, an object of a known shape is used as a standard object, with which the imaging operation by the fluorescence imaging unit and the imaging operation by the interference imaging unit are made to be carried out to acquire a three-dimensional fluorescence image and a three-dimensional interference image of the standard object, and wherein when there is a difference in relative position in the optical-axis direction between the three-dimensional fluorescence image and the three-dimensional interference image, the fluorescence imaging unit is moved in the optical-axis direction, thereby to finely adjust the optical system so as to eliminate the difference in relative position between the three-dimensional fluorescence image and the three-dimensional interference image, followed by execution of imaging of a variety of the observation objects.

8. The observation device according to claim 6, wherein at each of a plurality of target positions of the mount unit, an object of a known shape is used as a standard object, with which the imaging operation by the fluorescence imaging unit and the imaging operation by the interference imaging unit are made to be carried out to acquire a three-dimensional fluorescence image and a three-dimensional interference image of the standard object, and wherein when there is a difference in relative position in the optical-axis direction between the three-dimensional fluorescence image and the three-dimensional interference image, a lens which can be moved independently of a focusing condition of the interference image, out of lenses for focusing the fluorescence image, is moved in the optical-axis direction, thereby to finely adjust the optical system so as to eliminate the difference in relative position between the three-dimensional fluorescence image and the three-dimensional interference image, followed by execution of imaging of a variety of the observation objects.

9. The observation device according to claim 6, wherein the excitation light source and the fluorescence imaging unit have a configuration of a confocal microscope.

10. The observation device according to claim 6, wherein the excitation light source is a short pulse laser with a pulse duration of not more than 1000 femtoseconds, and wherein the excitation light source and the fluorescence imaging unit have a configuration of a two-photon excitation microscope.

11. The observation device according to claim 6, wherein the fluorescence imaging unit images fluorescence attributed to fluorescence resonance energy transfer in the observation object.

12. The observation device according to claim 6, wherein a granular object inside the observation object is fluorescently stained, and a plurality of three-dimensional fluorescence images and three-dimensional interference images of the observation object are taken in time series, to visualize a relative positional relation between the fluorescently-stained granular object and a film-like structure on a surface or inside of the observation object.

13. The observation device according to claim 6, wherein at a start of observation, the irradiation with the excitation light by the excitation light source is carried out and the imaging operation by the fluorescence imaging unit and the imaging operation by the interference imaging unit are carried out, only for a duration of time shorter than an overall time duration of observation, and correspondence is made between a fluorescently-labeled object and an object resulting from feature extraction by interference imaging, from images obtained by the operations, and wherein after completion of the imaging at the start of observation, the irradiation with the excitation light by the excitation light source is not carried out and only the imaging operation by the interference imaging unit is carried out, thereby to perform temporal observation of the fluorescently-labeled object.

* * * * *